US010450295B2

(12) United States Patent
Lee et al.

(10) Patent No.: US 10,450,295 B2
(45) Date of Patent: Oct. 22, 2019

(54) METHOD OF USING AN INDOLINONE MOLECULE AND DERIVATIVES FOR INHIBITING LIVER FIBROSIS AND HEPATITIS

(71) Applicant: Acclaim BioMed USA LLC, Sugar Land, TX (US)

(72) Inventors: Kenneth Ka-Ho Lee, Hong Kong (HK); Stanton Hon-Lung Kok, Hong Kong (HK); Tsz-Wai Kok, Hong Kong (HK); Sing-Wan Wong, Hong Kong (HK); John Yeuk-Hon Chan, Houston, TX (US)

(73) Assignee: Acclaim BioMed USA LLC, Sugar Land, TX (US)

( * ) Notice: Subject to any disclaimer, the term of this patent is extended or adjusted under 35 U.S.C. 154(b) by 1015 days.

(21) Appl. No.: 13/963,226

(22) Filed: Aug. 9, 2013

(65) Prior Publication Data

US 2015/0045395 A1    Feb. 12, 2015

(51) Int. Cl.

| | | |
|---|---|---|
| *C07D 209/34* | (2006.01) | |
| *C07D 209/40* | (2006.01) | |
| *C07D 401/06* | (2006.01) | |
| *C07D 401/12* | (2006.01) | |
| *C07D 405/12* | (2006.01) | |
| *A61K 31/404* | (2006.01) | |
| *A61K 31/4439* | (2006.01) | |
| *A61P 1/16* | (2006.01) | |

(52) U.S. Cl.
CPC ......... *C07D 401/06* (2013.01); *C07D 209/34* (2013.01); *C07D 209/40* (2013.01); *C07D 401/12* (2013.01); *C07D 405/12* (2013.01)

(58) Field of Classification Search
CPC .. C07D 401/06; C07D 209/34; C07D 209/40; C07D 401/12; C07D 405/12; A61K 31/404; A61K 31/4439

USPC ........................................... 514/418; 548/486
See application file for complete search history.

(56) References Cited

U.S. PATENT DOCUMENTS

| | | |
|---|---|---|
| 6,218,437 B1 * | 4/2001 | Chojkier ................. 514/731 |
| 2002/0010203 A1 * | 1/2002 | Lipson et al. ............ 514/418 |
| 2006/0142373 A1 * | 6/2006 | Park et al. ............... 514/414 |
| 2006/0148883 A1 | 7/2006 | Park et al. |
| 2006/0154993 A1 | 7/2006 | Park et al. |
| 2009/0048267 A1 | 2/2009 | Park et al. |
| 2010/0204211 A1 | 8/2010 | Park et al. |
| 2013/0035364 A1 * | 2/2013 | Go ..................... A61K 31/404 |
| | | 514/418 |

FOREIGN PATENT DOCUMENTS

WO    WO2002036564    5/2002

OTHER PUBLICATIONS

Dancygier Clinical Hepatology. Principles and Practice of Hepatobiliary Diseases, vol. 2, Springer-Verlag, Berlin 2010.*
Friedman, S. L. Physiol. Rev. 2008, 88, 125-172.*
Lin et al. Am. J. Physiol. Cell Physiol. 2011, 301, C469-477.*

* cited by examiner

*Primary Examiner* — Sreeni Padmanabhan
*Assistant Examiner* — Irina Neagu
(74) *Attorney, Agent, or Firm* — Harvest IP Law LLP

(57) ABSTRACT

This invention relates to methods of reversing and inhibiting liver fibrosis and hepatitis using a small indolinone molecule Hesperadin and related compounds. Methods of identifying such agents and using them to inhibit the expression of collagens and ECM proteins including MMPs and TIMPs in purified hepatic stellate cells are provided. In vivo data of Hesperadin in inhibiting induced collagen production are presented. This method of specifically targeting drugs to hepatic stellate cells in vivo, provides a novel therapy for liver diseases.

4 Claims, 31 Drawing Sheets
Specification includes a Sequence Listing.

Effect of Hesperadin on morphology of Human LX-2 Hepatic Stellate Cells (HSC)

Effect of Hesperadin on proliferation of LX-2 Hepatic Stellate Cell (48 hrs post-treatment)

Effect of Hesperadin on LX-2 HSC cell-cycle progression (48 hrs post-treatment)

Hesperadin suppressed collagen I protein expression in Human LX-2 HSC cells

Hesperadin suppressed collagen-IV protein expression in LX-2 HSC cells.

Hesperadin suppressed Collagen 3A1 gene expression in LX-2 cells by real-time RT-PCR Hesperadin supressed MMP-9 gene expression in LX-2 cells by real-time RT-PCR Hesperadin suppressed TIMP-1 gene expression in LX-2 by real-time RT-PCR

**Hesperadin suppressed liver fibrosis *in vivo***

Hesperadin (Z)-N-(2-oxo-3-(Phenyl((4-(piperidin-1-ylmethyl)phenyl)amino)methylene)
indolin-5-yl)ethanesulfonamide

MW = 516.65

(Z)-N-Cyclohexyl-2-(2-oxo-3-(phenyl(phenylamino)methylene)
indolin-1-yl)-2-phenylacetamide

MW = 527.66

(Z)-N-Cyclohexyl-2-(2-oxo-3-((phenylamino)methylene)indolin-1-yl)-2-phenylacetamide

MW=451.56

(Z)-3-Benzylideneindolin-2-one

MW=221.25

(Z)-3-(4-Fluorobenzylidene)indolin-2-one

MW=239.24

(Z)-3-(4-Chlorobenzylidene)indolin-2-one

MW=255.7

(Z)-3-(4-Bromobenzylidene)indolin-2-one

MW=300.15

(Z)-3-(4-Methoxybenzylidene)indolin-2-one

MW=251.28

(Z)-3-(4-(Dimethylamino)benzylidene) indolin-2-one

MW=264.32

(Z)-3-Benzylidene-5-bromoindolin-2-one

MW=300.15

IC50=31.25uM (Z)-3-(Pyridin-2-ylmethylene)indolin-2-one

MW=222.24

(Z)-5-Bromo-3-(pyridin-2-ylmethylene)indolin-2-one

MW=301.14

(Z)-3-((4-Chlorophenyl)imino)indolin-2-one

MW=256.69

IC50=62.5uM (Z)-3-((4-Bromophenyl)imino)indolin-2-one

MW=301.14

IC50=500uM (Z)-3-((4-Nitrophenyl)imino)indolin-2-one

MW=267.24

(Z)-3-(p-Tolylimino)indolin-2-one

MW=236.27

(Z)-3-(Pyridin-3-ylimino)indolin-2-one

MW=223.23

(Z)-3-((Furan-2-ylmethyl) imino)indolin-2-one

MW=226.23

IC50=125uM

METHOD OF USING AN INDOLINONE MOLECULE AND DERIVATIVES FOR INHIBITING LIVER FIBROSIS AND HEPATITIS

FIELD

Embodiments of the invention generally relate to methods and drugs to inhibit, reverse and treating liver diseases including liver fibrosis, hepatitis and cirrhosis.

BACKGROUND

Worldwide, liver diseases such as hepatitis, both viral and non-viral induced, are the primary causes of gastrointestinal (GI) disorders affecting hundreds of thousands of people (1-3). Hepatitis invariably leads to liver fibrosis, which may have drastic effects. Hepatitis virus infections including the hepatitis B virus (HBV) and the hepatitis C virus (HCV) are currently the major causes of liver diseases, which are endemic in many regions of the world (4-14). Many regions in the world, including the Western Pacific Region such as China, Taiwan, Hong Kong and Southeast Asia, are major endemic areas for hepatitis virus infections, which are mainly HBV and HCV (4-14).

In addition, chronic alcohol consumption, metabolic and autoimmune disorders, toxic/drug-induced injuries and biliary obstruction can also produce hepatitis and hepatic fibrosis. If liver fibrosis is left untreated, it can progress to overt liver cirrhosis and hepatic failure. Liver cirrhosis can also progress to primary hepatocellular carcinoma, which is one of the major malignancies in Africa and Asia, including China, Taiwan and Hong Kong. It is not surprising that liver disease is currently the 11th leading cause of death in the world (11-12). Furthermore, the rates of alcohol and drug abuses, which often leading to liver inflammation, in many immerging industrialized region are on the rise.

Liver fibrosis is formed as a consequence of continuous damage to the liver, caused by alcohol abuse, autoimmune diseases, drugs, metabolic diseases and viral hepatitis. The disease is characterized by excessive production and accumulation of extracellular matrix (ECM) proteins, which includes collagen types I, II, IV, V, VI and VII, fibronectin, undulin, elastin, laminin, hyaluronan and proteoglycans etc. The end stage of liver fibrosis is cirrhosis, which is characterized by: (a) extensive scar tissue formations, (b) the appearance of regenerative nodules accompanied by liver failure and (c) portal hypertension.

Liver fibrosis represents a tremendous worldwide healthcare problem. The biomarkers for liver fibrosis and hepatitis have been documented previously (8,9). Knowledge of the cellular and molecular mechanisms of liver fibrosis has now greatly advanced. Activated hepatic stellate cells (HSC), portal fibroblasts, and myofibroblasts of bone marrow origin have been identified as the major collagen-producing cells in the diseased liver (5,6). These cells are activated by fibrogenic cytokines such as TGF-beta1, angiotensin II, and leptin.

Recently, it has been reported that liver fibrosis could be reversed in patients, thus stimulating researchers to develop antifibrotic drugs. Emerging antifibrotic therapies are aimed at inhibiting the accumulation of fibrogenic cells and/or preventing the deposition of extracellular matrix proteins.

Therefore, it is important that drugs are developed specifically to target ECM producing cells such as activated HSC to combat liver fibrosis. In China, it has been estimated that the market value for medicines of liver disease is approximately 10 billion RMB, of which patented medicines in China account for 2 billion RMB. Statistics released by the Ministry of Chinese Public Health showed that the incidence of viral hepatitis including HBV and HCV in China is still very high and continues to rise. In 2010, the reported new cases for viral hepatitis in China were more than 1.3 million (13). There are approximately 120 million hepatitis sufferers in China that support the huge market of liver-disease medication.

At present, medicines for liver disease can be divided into several approaches. The main focus is on anti-viral medicines such as interferon, and ribavirin, a synthetic nucleoside analog that inhibits the viral genome duplication. In addition, lamivudine has been used for chronic hepatitis B infection, while treatment of hepatitis C and hepatitis D is with interferon and treatment of primary biliary cirrhosis is with methotrexate plus ursodiol.

According to the National Institutes of Health (NIH) of Bethesda, Md., USA, current treatments for HBV are interferons (interferon-α2b and peginterferon-α2a) and/or nucleoside or nucleotide analogues (lamivudine, adefovir, entecavir, Tenofovir Disoproxil Fumarate (TDF), telbivudine, Emtricitabine plus TDF and Truvada, (TVD) (8). The Current treatment for HCV infection is usually Peginterferon (PEG-IFN) Alfa-2b plus Ribavirin (RBV) (9).

However, the long-term usage of many of these drugs for HBV and HCV may develop drug-resistance, which is not beneficial to patients of chronic diseases. The administration of these drugs also requires long period of hospitalization and closed monitoring, which are costly and inconvenient. The world market for interferons alone was valued at US$3.8 billion in 2001. However, the cost of these treatments is enormously high and the effects are far from satisfactory. In addition, many of these patients are not eligible for liver transplant, and thus the prognosis for them is terribly ominous.

Recent research and developments have changed the dynamics of the treatment approach, and opened demands for medicine involved in reversing liver fibrosis, liver immunity regulation, and liver protection. It is interesting to note that one of the direct ways to treat liver disease and liver fibrosis is to inhibit the formation and the deposition of collagens and ECM. However, there is no product currently available that are effective in targeting the expression of collagens, ECM and limiting liver fibrosis. Thus, novel new drugs and methodologies are urgently needed to alleviate pains and sufferings of patients with hepatitis and liver fibrosis.

Hesperadin, an Aurora Kinase Inhibitor

To combat cancer and proliferative diseases, aurora kinase inhibitors are considered to be extremely useful because aurora kinases were found to be over-expressed in many types of cancer, and they could be responsible for the high proliferation and the loss of growth control in tumors (28-32). Small molecules that are aurora kinase inhibitors, such as Hesperadin, VX680 and reversine are good candidates for anti-cancer applications since they can be chemically produced, and are relatively stable, penetrable and permeable to various tissues and cells (28-42).

Hesperadin is a human Aurora B kinase inhibitor with a half maximal inhibitory concentration ("$IC_{50}$") of 40 nM for the prevention of the phosphorylation of substrate (40-55). Hesperadin blocks nuclear division and cytokinesis, but not other aspects of the cell cycle (40). Mammalian cells treated with Hesperadin enter anaphase in the presence of numerous mono-oriented chromosomes, many of which may have both sister kinetochores attached to one spindle pole (syntelic attachment) (40,45). Hesperadin also induced cells arrested by taxol or monastrol to enter anaphase within <1 h, whereas cells in nocodazole stayed arrested for 3-5 h. Moreover, the proper segregation of sister chromatids in mitosis depends on the bipolar attachment of all chromosomes to the mitotic spindle. Thus, Hesperadin has been identified as an effective inhibitor of chromosome alignment and segregation. Growth of cultured bloodstream forms (BF) was also sensitive to Hesperadin with an $IC_{50}$ of 50 nM (41).

These data implied that Hesperadin causes this phenotype by inhibiting the function of the mitotic kinase Aurora B (40). It suggested that Aurora B is required to generate unattached kinetochores on mono-oriented chromosomes, which in turn could promote bipolar attachment as well as maintain checkpoint signaling. Since the expression of aurora kinases were found to be up-regulated in many types of cancer, inhibitors of aurora kinases are thought to be extremely useful in combating neoplasia, proliferative and fibrotic diseases (28-32). Nevertheless, Hesperadin has not been documented for inhibiting liver fibrosis and hepatitis.

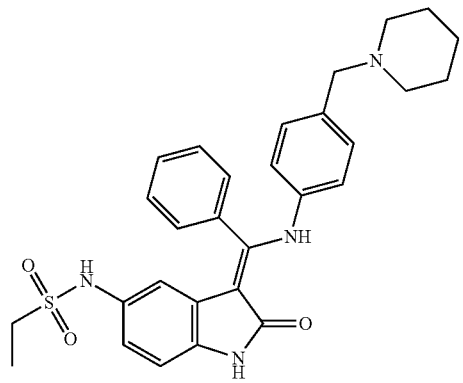

Chemical Structure of Herperadin

Moreover, Publication WO 2002/036564 A1 (Publication '564) of International Patent Application PCT/EP2001/012523 describes indolinone derivatives including Hesperadin that are directed to the inhibition of the proliferation of tumor cells and protein kinases (60). However, Publication '564 does not describe the use of Hesperadin and related indolinones therein as inhibitors of liver fibrosis or inflammation.

Indolinone Derivatives for Fibrotic Diseases

Several U.S. patent application publications have reported using indolinone derivatives to treat fibrotic diseases (55-59). For instance, U.S. Patent Publications 2006/0142373 A1 (Publication '373), 2006/0148883 A1 (Publication '883), and 2006/0154939 A1 (Publication '939), utilize indolinones that can be represented by the following general formula for fibrotic diseases:

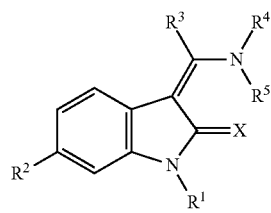

wherein $R^1$, $R^2$, $R^3$, $R^4$, $R^5$ and $R^6$ are defined. Because the substitution at position 5 of the indolinone is $R^6$, which is hydrogen, the indolinones in Publications '373, '883 and '939 are structurally different and not related to Hesperadin. In addition, Publications '373, '883 and '939 do not describe the indolinones therein as biologically active against hepatic stellate cells (HSC).

On the other hand, U.S. Patent Publications 2009/0048267 A1 (Publication '267) and 2010/0204211 A1 (Publication '211) also utilize indolinones that can be represented by the following general formula for fibrotic diseases:

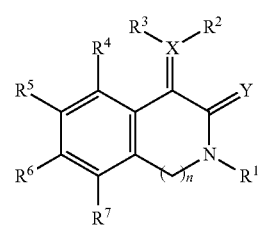

wherein $R^1$, $R^2$, $R^3$, $R^4$, and $R^5$ are defined. Because position 5 of the indolinone is hydrogen, the indolinones in Publications '267 and '211 are structurally different and not related to Hesperadin. Furthermore, Publications '267 and '211 only presented biological activities related to bleomycin-induced lung fibrosis, and Publication '267 also describes virally induced hepatic cirrhosis. However, Publications '267 and '211 do not describe the indolinones therein as biologically active against hepatic stellate cells (HSC).

Therefore, there remains a need to utilize indolinones that are structurally related to Hesperadin but are capable of inhibiting hepatic stellate cells (HSC) as treatments of liver fibrosis and hepatitis.

SUMMARY

In accordance to an embodiment of the invention, a method for treating a condition associated with a liver disease includes the steps of: (1) preparing a compound having a structure according to Formulas I:

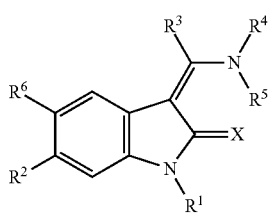

Formula I wherein X is carbon or nitrogen, Y is oxygen or sulfur; n is 0 or 1; $R^1$, $R^2$, $R^3$, $R^4$, $R^5$, $R^6$, $R^7$ are independently H, $CH_2R^8$, $CHR^9R^{10}$, $CR^{11}R^{12}R^{13}$, $C(O)OR^{14}$, $C(O)R^{15}$, $C(O)NR^{16}R^{17}$, $NR^{18}C(O)R^{19}$, N—$R^{20}R^{21}$, O—$R^{22}$, S—$R^{22}$, $SO_2R^{23}$, $SO_3R^{24}$, $NSO_2R^{25}$, F, Cl, Br, I, aromatic, heteroaromatic, and $R^8$-$R^{25}$ are independently hydrogen, amino, $C_{1-12}$-alkyl, -aryl, heteroaryl or bioactive polymer, or a tautomer, a stereoisomer or a pharmaceutically acceptable salt or ester thereof; (2) administering effective amount of the compound to a subject having the condition associated with the liver disease; (3) targeting hepatic stellate cells of the subject; (4) inhibiting synthesis or expression of at least one collagen or extra cellular matrix proteins; and (5) reversing the condition associated with the liver disease.

In an embodiment of the invention, the compound utilized in the method of treating the condition associated with the liver disease has a structural according to Formula I, wherein X is carbon, n is 0, $R^5$ is $NSO_2$—$C_2H_5$, and is a member selected from the group consisting of:
(Z)—N-(2-oxo-3-(Phenyl(4-(piperidin-1-ylmethyl)phenylamino)methylene)indolin-5-yl)ethanesulfonamide (Hesperadin)
(Z)—N-(2-oxo-3-(Phenyl(phenylamino)methylene)indolin-5-yl)ethanesulfonamide
(Z)—N-(2-oxo-3-(Phenyl(p-tolylamino)methylene)indolin-5-yl)ethanesulfonamide
(Z)—N-(3-((4-Methoxyphenylamino)(phenyl)methylene)-2-oxoindolin-5-yl)ethanesulfonamide
(Z)—N-(3-((4-(Dimethylamino)phenylamino)(phenyl)methylene)-2-oxoindolin-5-yl)ethanesulfonamide
(Z)—N-(3-((4-Fluorophenylamino)(phenyl)methylene)-2-oxoindolin-5-yl)ethanesulfonamide
(Z)—N-(3-((4-Chlorophenylamino)(phenyl)methylene)-2-oxoindolin-5-yl)ethanesulfonamide
(Z)—N-(3-((4-Bromophenylamino)(phenyl)methylene)-2-oxoindolin-5-yl)ethanesulfonamide
(Z)—N-(3-((4-Nitrophenylamino)(phenyl)methylene)-2-oxoindolin-5-yl)ethanesulfonamide
(Z)—N-(3-((4-(Morpholinomethyl)phenylamino)(phenyl)methylene)-2-oxoindolin-5-yl)ethanesulfonamide
(Z)—N-(3-(Diphenylmethylene)-2-oxoindolin-5-yl)ethanesulfonamide
(Z)—N-(2-oxo-3-(Phenyl(p-tolyl)methylene)indolin-5-yl)ethanesulfonamide
(Z)—N-(3-((4-methoxyphenyl)(phenyl)methylene)-2-oxoindolin-5-yl)ethanesulfonamide
(Z)—N-(3-((4-(Dimethylamino)phenyl)(phenyl)methylene)-2-oxoindolin-5-yl)ethanesulfonamide
(Z)—N-(3-((4-Fluorophenyl)(phenyl)methylene)-2-oxoindolin-5-yl)ethanesulfonamide
(Z)—N-(3-((4-Chlorophenyl)(phenyl)methylene)-2-oxoindolin-5-yl)ethanesulfonamide
(Z)—N-(3-((4-Bromophenyl)(phenyl)methylene)-2-oxoindolin-5-yl)ethanesulfonamide
(Z)—N-(3-((4-Nitrophenyl)(phenyl)methylene)-2-oxoindolin-5-yl)ethanesulfonamide
(Z)—N-(2-oxo-3-(Phenyl(4-(piperidin-1-ylmethyl)phenyl)methylene)indolin-5-yl)ethanesulfonamide
(Z)—N-(3-((4-(Morpholinomethyl)phenyl)(phenyl)methylene)-2-oxoindolin-5 yl)ethanesulfonamide
(Z)—N-(3-Benzylidene-2-oxoindolin-5-yl)ethanesulfonamide
(Z)—N-(3-(4-Methylbenzylidene)-2-oxoindolin-5-yl)ethanesulfonamide
(Z)—N-(3-(4-Methoxybenzylidene)-2-oxoindolin-5-yl)ethanesulfonamide
(Z)—N-(3-(4-(Dimethylamino)benzylidene)-2-oxoindolin-5-yl)ethanesulfonamide
(Z)—N-(3-(4-Fluorobenzylidene)-2-oxoindolin-5-yl)ethanesulfonamide
(Z)—N-(3-(4-Chlorobenzylidene)-2-oxoindolin-5-yl)ethanesulfonamide
(Z)—N-(3-(4-Bromobenzylidene)-2-oxoindolin-5-yl)ethanesulfonamide
(Z)—N-(3-(4-Nitrobenzylidene)-2-oxoindolin-5-yl)ethanesulfonamide
(Z)—N-(2-oxo-3-(4-(Piperidin-1-ylmethyl)benzylidene)indolin-5-yl)ethanesulfonamide
(Z)—N-(3-(4-(Morpholinomethyl)benzylidene)-2-oxoindolin-5-yl)ethanesulfonamide
(Z)—N-(2-oxo-3-(Phenylimino)indolin-5-yl)ethanesulfonamide
(Z)—N-(2-oxo-3-(p-Tolylimino)indolin-5-yl)ethanesulfonamide
(Z)—N-(3-((4-Methoxyphenyl)imino)-2-oxoindolin-5-yl)ethanesulfonamide
(Z)—N-(3-((4-(Dimethylamino)phenyl)imino)-2-oxoindolin-5-yl)ethanesulfonamide
(Z)—N-(3-((4-Fluorophenyl)imino)-2-oxoindolin-5-yl)ethanesulfonamide
(Z)—N-(3-((4-Chlorophenyl)imino)-2-oxoindolin-5-yl)ethanesulfonamide
(Z)—N-(3-((4-Bromophenyl)imino)-2-oxoindolin-5-yl)ethanesulfonamide
(Z)—N-(3-((4-Nitrophenyl)imino)-2-oxoindolin-5-yl)ethanesulfonamide
(Z)—N-(2-oxo-3-((4-(Piperidin-1-ylmethyl)phenyl)imino)indolin-5-yl)ethanesulfonamide and
(Z)—N-(3-((4-(Morpholinomethyl)phenyl)imino)-2-oxoindolin-5-yl)ethanesulfonamide.

In an embodiment of the invention, the compound utilized in the method of treating the condition associated with the liver disease has a structural according to Formula I, wherein X is carbon, n is 0, $R^4$ is H, $R^5$ is H or Br, $R^6$ is H, $R^7$ is H, and the compound is a member of the group consisting of:
(Z)—N-Cyclohexyl-2-(2-oxo-3-(phenyl(phenylamino)methylene)indolin-1-yl)-2-phenylacetamide
(Z)—N-Cyclohexyl-2-(2-oxo-3-((phenylamino)methylene)indolin-1-yl)-2-phenylacetamide
(Z)-3-Benzylideneindolin-2-one
(Z)-3-(4-Fluorobenzylidene)indolin-2-one
(Z)-3-(4-Chlorobenzylidene)indolin-2-one
(Z)-3-(4-Bromobenzylidene)indolin-2-one
(Z)-3-(4-Methoxybenzylidene)indolin-2-one
(Z)-3-(4-Dimethylamino)benzylidene)indolin-2-one
(Z)-3-Benzylidene-5-bromoindolin-2-one
(Z)-3-(Pyridin-2-ylmethylene)indolin-2-one and
(Z)-5-Bromo-3-(pyridin-2-ylmethylene)indolin-2-one.

In an embodiment of the invention, the compound utilized in the method of treating the condition associated with the liver disease has a structural according to Formula I, wherein X is nitrogen, n is 0, $R^4$ is H, $R^5$ is H or Br, $R^6$ is H, $R^7$ is H, and the compound is a member of the group consisting of:
(Z)-3-((4-Chlorophenyl)imino)indolin-2-one
(Z)-3-((4-Bromophenyl)imino)indolin-2-one
(Z)-3-((4-Nitrophenyl)imino)indolin-2-one
(Z)-3-(p-Tolylimino)indolin-2-one
(Z)-3-(Pyridin-3-ylimino)indolin-2-one and
(Z)-3-((Furan-2-ylmethyl)imino)indolin-2-one.

In an embodiment of the invention, the compound utilized in the method of treating the condition associated with the liver disease is Hesperadin, which is (Z)—N-(2-oxo-3-(Phenyl(4-(piperidin-1-ylmethyl)phenylamino)methylene)indolin-5-yl)ethanesulfonamide.

In an embodiment of the invention, the liver disease to be treated by the method is a member selected from the group consisting of hepatitis due to hepatitis B virus, hepatitis due to hepatitis C virus, hepatitis due to chronic alcohol consumption, hepatitis due to metabolic disorder, hepatitis due to autoimmune disorder, hepatitis due to drug-induced injury, hepatitis due to biliary obstruction, liver fibrosis and cirrhosis.

In an embodiment of the invention, the at least one collagen that is being inhibited by the method is selected from the group consisting of collagen type I, collagen type III, collagen type IV, collagen type V, collagen type VI and collagen type VII.

In an embodiment of the invention, the compound utilized in the method of treating the condition associated with the liver disease is Hesperadin, which is (Z)—N-(2-oxo-3-(Phenyl(4-(piperidin-1-ylmethyl)phenylamino)methylene)indolin-5-yl)ethanesulfonamide, and the liver disease to be treated by the method is a member selected from the group consisting of hepatitis due to hepatitis B virus, hepatitis due to hepatitis C virus, hepatitis due to chronic alcohol consumption, hepatitis due to metabolic disorder, hepatitis due to autoimmune disorder, hepatitis due to drug-induced injury, hepatitis due to biliary obstruction, liver fibrosis and cirrhosis.

In an embodiment of the invention, the compound utilized in the method of treating the condition associated with the liver disease is Hesperadin, which is (Z)—N-(2-oxo-3-(Phenyl(4-(piperidin-1-ylmethyl)phenylamino)methylene)indolin-5-yl)ethanesulfonamide, and the at least one collagen that is being inhibited by the method is selected from the group consisting of collagen type I, collagen type III, collagen type IV, collagen type V, collagen type VI and collagen type VII.

In an embodiment of the invention, a pharmacological composition for treating a condition associated with a liver disease includes a compound having a structure according to Formula I:

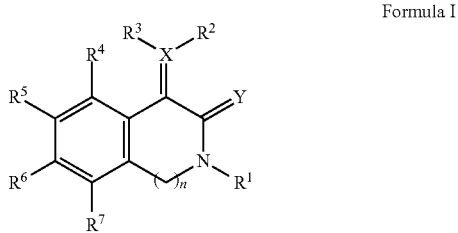

Formula I wherein X is carbon or nitrogen, Y is oxygen or sulfur; n is 0 or 1; $R^1$, $R^2$, $R^3$, $R^4$, $R^5$, $R^6$, $R^7$ are independently H, $CH_2R^8$, $CHR^9R^{10}$, $CR^{11}R^{12}R^{13}$, $C(O)OR^{14}$, $C(O)R^{15}$, $C(O)NR^{16}R^{17}$, $NR^{18}C(O)R^{19}$, N—$R^{20}R^{21}$, O—$R^{22}$, S—$R^{22}$, $SO_2R^{23}$, $SO_3R_{24}$, $NSO_2R^{25}$, F, Cl, Br, I, aromatic, heteroaromatic, and $R^8$-$R^{25}$ are independently hydrogen, amino, $C_{1-12}$-alkyl, -aryl, heteroaryl or bioactive polymer, or a tautomer, a stereoisomer or a pharmaceutically acceptable salt or ester thereof; whereby the pharmacological composition is capable of targeting hepatic stellate cells of the subject, inhibiting synthesis or expression of at least one collagen or extra cellular matrix proteins; and reversing the condition associated with the liver disease.

BRIEF DESCRIPTION OF THE DRAWINGS

Embodiments of the invention will be more clearly understood by reference to the following detailed description and the accompanying drawings in which.

DETAILED DESCRIPTION OF THE EMBODIMENTS

Figure 1:
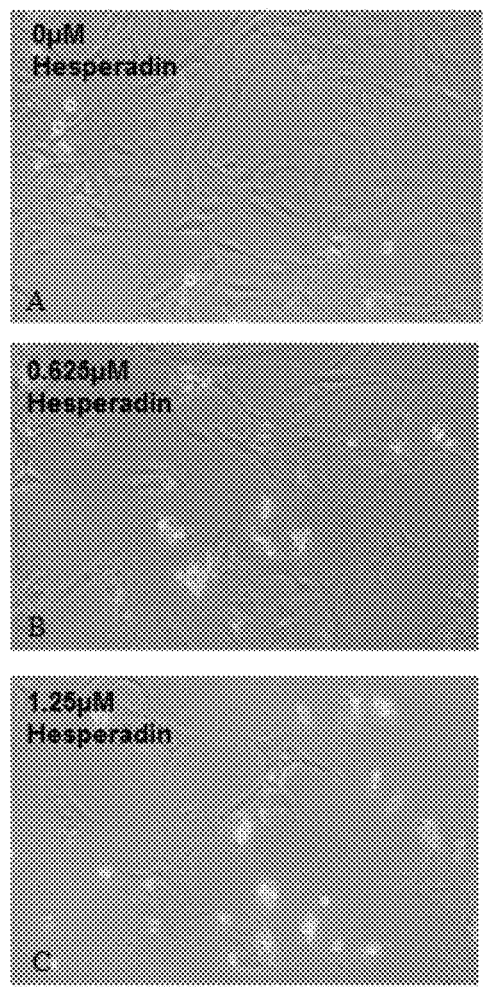
FIG. 1 is a collection of images A, B and C of human hepatic stellate cells (HSC's) under the microscope, showing the effect of Hesperadin on the morphology of HSC's. Images A-C show the morphology of human HSC's (LX-2) cultured in the presence of Hesperadin for 24 hours at concentrations of 0, 0.65 and 1.25 µM, respectively. The HSC's increased in size by several folds in the presence of Hesperadin.

In accordance to the first aspect of the invention, a method of treating a condition associated with a liver disease includes the steps of: (1) preparing a compound; (2) administering an effective amount of the compound to a subject having the condition associated with the liver disease; (3) targeting hepatic stellate cells of the subject; (4) inhibiting synthesis or expression of at least one collagen or extra cellular matrix proteins; and (5) reversing the condition associated with the liver disease. The compound has a structural according to Formula I:

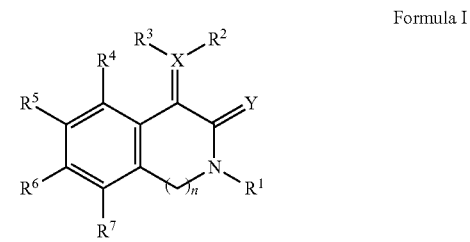

Formula I wherein X is carbon or nitrogen, Y is oxygen or sulfur; n is 0 or 1; $R^1$, $R^2$, $R^3$, $R^4$, $R^5$, $R^6$, $R^7$ are independently H, $CH_2R^8$, $CHR^9R^{10}$, $CR^{11}R^{12}R^{13}$, $C(O)OR^{14}$, $C(O)R^{15}$, $C(O)NR^{16}R^{17}$, $NR^{18}C(O)R^{19}$, $N-R^{20}R^{21}$, $O-R^{22}$, $S-R^{22}$, $SO_2R^{23}$, $SO_3R^{24}$, $NSO_2R^{25}$, F, Cl, Br, I, aromatic, heteroaromatic, and $R^8$-$R^{25}$ are independently hydrogen, amino, $C_{1-12}$-alkyl, -aryl, heteroaryl or bioactive polymer, or a tautomer, a stereoisomer or a pharmaceutically acceptable salt or ester thereof.

In accordance to the second aspect of the invention, a pharmacological composition for treating a condition associated with a liver disease includes a compound having a structure according to Formula I:

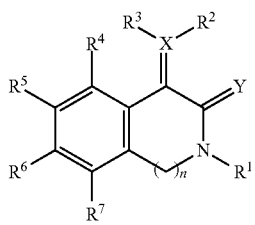

Formula I wherein X is carbon or nitrogen, Y is oxygen or sulfur; n is 0 or 1; R1, R2, R3, R4, R5, R6, R7 are independently H, $CH_2R^8$, $CHR^9R^{10}$, $CR^{11}R^{12}R^{13}$, $C(O)OR^{14}$, $C(O)R^{15}$, $C(O)NR^{16}R^{17}$, $NR^{18}C(O)R^{19}$, $N-R^{20}R^{21}$, $O-R^{22}$, $S-R^{22}$, $SO_2R^{23}$, $SO_3R^{24}$, $NSO_2R^{25}$, F, Cl, Br, I, aromatic, heteroaromatic, and $R^8$-$R^{25}$ are independently hydrogen, amino, $C_{1-12}$-alkyl, -aryl, heteroaryl or bioactive polymer, or a tautomer, a stereoisomer or a pharmaceutically acceptable salt or ester thereof; whereby the pharmacological composition is capable of targeting hepatic stellate cells of the subject, inhibiting synthesis or expression of at least one collagen or extra cellular matrix proteins; and reversing the condition associated with the liver disease.

The inventors' research group has been interested in the molecular pathways and therapy of liver diseases and hepatocellular carcinoma (HCC) (16-27), and has reported the up-regulated expression of an anti-apoptotic gene BRE in HCC and liver diseases (19, 20). The inventors used Reversine to inhibit or reverse liver fibrosis or hepatitis (27), and reported on the effect of a Chinese herbal medicine on a liver-damage model (25, 26). In contrast, the present patent application focuses on using an indolinone molecule related to Hesperadin for inhibiting fibrosis and hepatitis.

Method of Treating Liver Diseases

Step (1) Preparing A Compound

Accordingly, a method for treating a subject suffering from a disease or a condition associated with viral or non-viral hepatitis, liver fibrosis, cirrhosis and liver cancer includes the step of preparing a small molecule having a structure according to Formula I:

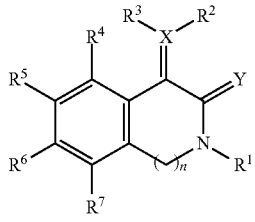

Formula I wherein X is carbon or nitrogen, Y is oxygen or sulfur; n is 0 or 1; $R^1$, $R^2$, $R^3$, $R^4$, $R^5$, $R^6$, $R^{14}$ are independently H, $CH_2R^8$, $CHR^9R^{10}$, $CR^{11}R^{12}R^{13}$, $C(O)OR^{14}$, $C(O)R^{15}$, $C(O)NR^{16}R^{17}$, $NR^{18}C(O)R^{19}$, $N-R^{20}R^{21}$, $O-R^{22}$, $S-R^{22}$, $SO_2R^{23}$, $SO_3R^{24}$, $NSO_2R^{25}$, F, Cl, Br, I, aromatic, heteroaromatic, and $R^8$-$R^{25}$ are independently hydrogen, amino, $C_{1-12}$-alkyl, -aryl, heteroaryl or bioactive polymer, or a tautomer, a stereoisomer or a pharmaceutically acceptable salt or ester thereof. The general methods of preparing these compounds are described in further details in Examples 1 and 2 below.

In an embodiment of the invention, the compound utilized in the method of treating the condition associated with the liver disease has a structural according to Formula I, wherein X is carbon, n is 0, $R^5$ is $NSO_2$—$C_2H_5$, and is a member selected from the group consisting of:

Hesperadin, ((Z)—N-(2-oxo-3-(Phenyl(4-(piperidin-1-ylmethyl)phenylamino)methylene)indolin-5-yl)ethanesulfonamide).

(Z)—N-(2-oxo-3-(Phenyl(phenylamino)methylene)indolin-5-yl)ethanesulfonamide (Z)—N-(2-oxo-3-(Phenyl(p-tolylamino)methylene)indolin-5-yl)ethanesulfonamide (Z)—N-(3-((4-Methoxyphenylamino)(phenyl)methylene)-2-oxoindolin-5-yl)ethanesulfonamide (Z)—N-(3-((4-(Dimethylamino)phenylamino)(phenyl)methylene)-2-oxoindolin-5-yl)ethanesulfonamide (Z)—N-(3-((4-Fluorophenylamino)(phenyl)methylene)-2-oxoindolin-5-yl)ethanesulfonamide (Z)—N-(3-((4-Chlorophenylamino)(phenyl)methylene)-2-oxoindolin-5-yl)ethanesulfonamide (Z)—N-(3-((4-Bromophenylamino)(phenyl)methylene)-2-oxoindolin-5-yl)ethanesulfonamide (Z)—N-(3-((4-Nitrophenylamino)(phenyl)methylene)-2-oxoindolin-5-yl)ethanesulfonamide (Z)—N-(3-((4-(Morpholinomethyl)phenylamino)(phenyl)methylene)-2-oxoindolin-5-yl)ethanesulfonamide (Z)—N-(3-(Diphenylmethylene)-2-oxoindolin-5-yl)ethanesulfonamide (Z)—N-(2-oxo-3-(Phenyl(p-tolyl)methylene)indolin-5-yl)ethanesulfonamide (Z)—N-(3-((4-Methoxyphenyl)(phenyl)methylene)-2-oxoindolin-5-yl)ethanesulfonamide (Z)—N-(3-((4-(Dimethylamino)phenyl)(phenyl)methylene)-2-oxoindolin-5-yl)ethanesulfonamide (Z)—N-(3-((4-Fluorophenyl)(phenyl)methylene)-2-oxoindolin-5-yl)ethanesulfonamide (Z)—N-(3-((4-Chlorophenyl)(phenyl)methylene)-2-oxoindolin-5-yl)ethanesulfonamide (Z)—N-(3-((4-Bromophenyl)(phenyl)methylene)-2-oxoindolin-5-yl)ethanesulfonamide (Z)—N-(3-((4-Nitrophenyl)(phenyl)methylene)-2-oxoindolin-5-yl)ethanesulfonamide (Z)—N-(2-oxo-3-(Phenyl(4-(piperidin-1-ylmethyl)phenyl)methylene)indolin-5-yl)ethanesulfonamide (Z)—N-(3-((4-(Morpholinomethyl)phenyl)(phenyl)methylene)-2-oxoindolin-5 yl)ethanesulfonamide (Z)—N-(3-Benzylidene-2-oxoindolin-5-yl)ethanesulfonamide (Z)—N-(3-(4-Methylbenzylidene)-2-oxoindolin-5-yl)ethanesulfonamide (Z)—N-(3-(4-Methoxybenzylidene)-2-oxoindolin-5-yl)ethanesulfonamide (Z)—N-(3-(4-(Dimethylamino)benzylidene)-2-oxoindolin-5-yl)ethanesulfonamide (Z)—N-(3-(4-Fluorobenzylidene)-2-oxoindolin-5-yl)ethanesulfonamide (Z)—N-(3-(4-Chlorobenzylidene)-2-oxoindolin-5-yl)ethanesulfonamide (Z)—N-(3-(4-Bromobenzylidene)-2-oxoindolin-5-yl)ethanesulfonamide (Z)—N-(3-(4-Nitrobenzylidene)-2-oxoindolin-5-yl)ethanesulfonamide (Z)—N-(2-oxo-3-(4-(Piperidin-1-ylmethyl)benzylidene)indolin-5-yl)ethanesulfonamide (Z)—N-(3-(4-(Morpholinomethyl)benzylidene)-2-oxoindolin-5-yl)ethanesulfonamide (Z)—N-(2-oxo-3-(Phenylimino)indolin-5-yl)ethanesulfonamide (Z)—N-(2-oxo-3-(p-Tolylimino)indolin-5-yl)ethanesulfonamide (Z)—N-(3-((4-Methoxyphenyl)imino)-2-oxoindolin-5-yl)ethanesulfonamide (Z)—N-(3-((4-(Dimethylamino)phenyl)imino)-2-oxoindolin-5-yl)ethanesulfonamide (Z)—N-(3-((4-Fluorophenyl)imino)-2-oxoindolin-5-yl)ethanesulfonamide (Z)—N-(3-((4-Chlorophenyl)imino)-2-oxoindolin-5-yl)ethanesulfonamide (Z)—N-(3-((4-Bromophenyl)imino)-2-oxoindolin-5-yl)ethanesulfonamide (Z)—N-(3-((4-Nitrophenyl)imino)-2-oxoindolin-5-yl)ethanesulfonamide (Z)—N-(2-oxo-3-((4-(Piperidin-1-ylmethyl)phenyl)imino)indolin-5-yl)ethanesulfonamide and (Z)—N-(3-((4-(Morpholinomethyl)phenyl)imino)-2-oxoindolin-5-yl)ethanesulfonamide.

In another embodiment of the invention, the compound utilized in the method of treating the condition associated with the liver disease has a structural according to Formula I, wherein X is carbon, n is 0, $R^4$ is H, $R^5$ is H or Br, $R^6$ is H, $R^7$ is H, and the compound is a member of the group consisting of:

(Z)—N-Cyclohexyl-2-(2-oxo-3-(phenyl(phenylamino)methylene)indolin-1-yl)-2-phenylacetamide (Z)—N-Cyclohexyl-2-(2-oxo-3-((phenylamino)methylene)indolin-1-yl)-2-phenylacetamide (Z)-3-Benzylideneindolin-2-one (Z)-3-(4-Fluorobenzylidene)indolin-2-one (Z)-3-(4-Chlorobenzylidene)indolin-2-one (Z)-3-(4-Bromobenzylidene)indolin-2-one (Z)-3-(4-Methoxybenzylidene)indolin-2-one (Z)-3-(4-(Dimethylamino)benzylidene)indolin-2-one (Z)-3-Benzylidene-5-bromoindolin-2-one (Z)-3-(Pyridin-2-ylmethylene)indolin-2-one and (Z)-5-Bromo-3-(pyridin-2-ylmethylene)indolin-2-one.

In a different embodiment of the invention, the compound utilized in the method of treating the condition associated with the liver disease has a structural according to Formula I, wherein X is nitrogen, n is 0, $R^4$ is H, $R^5$ is H or Br, $R^6$ is H, $R^7$ is H, and the compound is a member of the group consisting of:

(Z)-3-((4-Chlorophenyl)imino)indolin-2-one (Z)-3-((4-Bromophenyl)imino)indolin-2-one (Z)-3-((4-Nitrophenyl)imino)indolin-2-one (Z)-3-(p-Tolylimino)indolin-2-one (Z)-3-(Pyridin-3-ylimino)indolin-2-one and (Z)-3-((furan-2-ylmethyl)imino)indolin-2-one.

Preferably, the compound that is useful as part of the method of the invention is Hesperadin, which is (Z)—N-(2-oxo-3-(Phenyl(4-(piperidin-1-ylmethyl)phenylamino)methylene)indolin-5-yl)ethanesulfonamide.

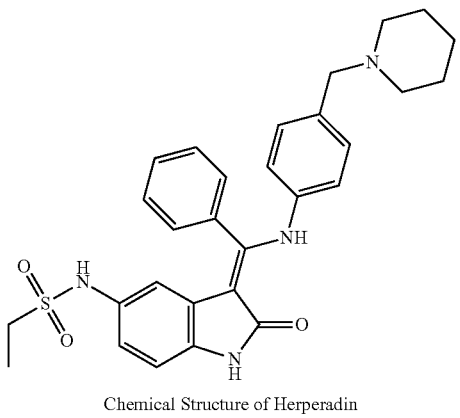 [SMILES: CCS(=O)(=O)Nc1ccc2c(c1)/C(=C(/Nc1ccc(CN3CCCCC3)cc1)c1ccccc1)C(=O)N2]

Chemical Structure of Herperadin

The selection of compounds to be used is carried out by evaluating the biological activities of the compounds against HSC cells. Further discussion of the biological activities is reported below.

Step (2) Administering Effective Amount of Compound to Subject

Compositions and Methods for Administration

Another step of the method to treat the condition associated with liver disease is related to administering an effective amount of the compound to a subject having the condition associated with the liver disease. The administering step may include using a suitable pharmaceutical formulation to deliver the compound to the subject who shows the conditions of liver disease. The pharmaceutical formulation for the treatment, prophylaxis, and amelioration of proliferative disorders and fibrosis may include the compound compositions in the form of a pill, a tablet, a capsule, a liquid solution, a liquid suspension, a powder, or an intravenous solution with one or more pharmaceutically acceptable carriers or excipients or a pharmaceutically acceptable dosage formulation. The compounds compositions may be in form of dietary supplement or food additives including a prophylactically or therapeutically effective amount of one or more prophylactic or therapeutic agents. Additional information may be found in U.S. Patent Publication 2010/0273840 (64).

Dosage & Frequency of Administration

The dosage of administration is the amount of the compound in an appropriate composition to maintain optimal levels in prevention, treatment, relief, or amelioration of adverse health condition, a disorder, or one or more symptoms thereof. Thus, the dosage may vary with the nature and severity of the disease or condition. Also, the efficacy of the compound and composition is dependent on the route and/or the frequency of administration under specific factors for each subject or patient (e.g. age, body weight, response, the past medical history, etc.). Effective doses may be extrapolated from dose-response curves derived from in vitro or animal model testing systems (64).

Step (3) Targeting Hepatic Stellate Cells (HSC's)

According to the method to treat the condition associated with the liver disease, another step is related to targeting the compound to hepatic stellate cells (HSC's). The hepatic stellate cells are present in the sinusoidal spaces of the liver, and they are recognized to play a major role in the formation of fibrosis. Hepatic stellate cells are the major cells to produce collagens and proteins of extra-cellular matrix (ECM), which are critical for the fibrosis process. Therefore, it is important that the effective amount of the compound to treat the condition associated with liver disease should be present at the hepatic stellate cells.

In addition, this method of targeting the compound to hepatic stellate cells may be further enhanced by using a therapeutically effective amount of an indolinone compound related to Hesperadin that is encapsulated or linked to vitamin A or retinoic acid coated liposomes or other carriers. This approach of encapsulating or linking Hesperadin or related compounds to vitamin A or retinoic acid coated liposomes to target hepatic stellate cells (HSC) and other fibrotic cells increases the efficacy of Hesperadin and related compounds.

Step 4 Inhibiting Synthesis or Expression of Collagens or Extra Cellular Matrix Proteins According to the method to treat the condition associated with the liver disease, another step is related to inhibiting or reversing the synthesis or expression of collagens and Extra Cellular Matrix (ECM) proteins including MMPs and TIMPs or related signaling molecules in liver. The collagens that can be inhibited include collagen type I, collagen type III, collagen type IV, collagen type V, collagen type VI and collagen type VII.

The reversion or inhibition of these molecules is an indication of the successful inhibiting or reversing liver fibrosis and hepatitis, which are the precursor stages of developing into liver cirrhosis and HCC.

Vitamin A and retinoic acid are used in this instance as baits because the hepatic stellate cells in the liver normally function by absorbing vitamin A from the blood and storing it. In this manner, Hesperadin targets specifically into activated hepatic stellate cells in vivo, and inhibiting them from over-producing collagens and other ECM. It will be able to reduce the optimal concentration of Hesperadin required for it to be effective (i.e. compared with Hesperadin directly injected into the blood stream) and to increase its efficacy.

Therefore, according to the method of the invention, conditions associated with liver diseases can be treated. The type of liver disease includes hepatitis due to hepatitis B virus, hepatitis due to hepatitis C virus, hepatitis due to chronic alcohol consumption, hepatitis due to metabolic disorder, hepatitis due to autoimmune disorder, hepatitis due to drug-induced injury, hepatitis due to biliary obstruction, liver fibrosis and cirrhosis.

In an embodiment of the invention, the compound utilized in the method of treating the condition associated with the liver disease is Hesperadin, and the type of liver disease to be treated by the method includes hepatitis due to hepatitis B virus, hepatitis due to hepatitis C virus, hepatitis due to chronic alcohol consumption, hepatitis due to metabolic disorder, hepatitis due to autoimmune disorder, hepatitis due to drug-induced injury, hepatitis due to biliary obstruction, liver fibrosis and cirrhosis.

In an embodiment of the invention, the compound utilized in the method of treating the condition associated with the liver disease is Hesperadin, and the at least one collagen that is being inhibited by the method includes collagen type I, collagen type III, collagen type IV, collagen type V, collagen type VI and collagen type VII.

In accordance to a different aspect of the invention, a pharmacological composition for treating a condition associated with a liver disease includes a compound having a structure according to Formula I:

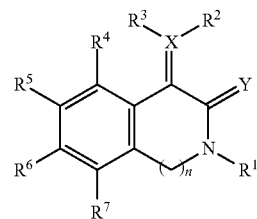

Formula I wherein X is carbon or nitrogen, Y is oxygen or sulfur; n is 0 or 1; $R^1$, $R^2$, $R^3$, $R^4$, $R^5$, $R^6$, $R^7$ are independently H, $CH_2R^8$, $CHR^9R^{10}$, $CR^{11}R^{12}R^{13}$, $C(O)OR^{14}$, $C(O)R^{15}$, $C(O)NR^{16}R^{17}$, $NR^{18}C(O)R^{19}$, $N-R^{20}R^{21}$, $O-R^{22}$, $S-R^{22}$, $SO_2R^{23}$, $SO_3R^{24}$, $NSO_2R^{25}$, F, Cl, Br, I, aromatic, heteroaromatic, and $R^8$-$R^{25}$ are independently hydrogen, amino, $C_{1-12}$-alkyl, -aryl, heteroaryl or bioactive polymer, or a tautomer, a stereoisomer or a pharmaceutically acceptable salt or ester thereof.

In addition, the pharmacological composition is capable of (1) targeting hepatic stellate cells of the subject, (2) inhibiting synthesis or expression of at least one collagen or extra cellular matrix proteins; and (3) reversing the condition associated with the liver disease.

In an embodiment of the invention, in the pharmacological composition for treating a condition associated with the liver disease, the compound that can be used has a structural according to Formula I, wherein X is carbon, n is 0, $R^5$ is $NSO_2$—$C_2H_5$, and is a member selected from the group consisting of:

(Z)—N-(2-oxo-3-(Phenyl(4-(piperidin-1-ylmethyl)phenylamino)methylene)indolin-5-yl)ethanesulfonamide (Hesperadin)

(Z)—N-(2-oxo-3-(Phenyl(phenylamino)methylene)indolin-5-yl)ethanesulfonamide (Z)—N-(2-oxo-3-(Phenyl(p-tolylamino)methylene)indolin-5-yl)ethanesulfonamide (Z)—N-(3-((4-Methoxyphenylamino)(phenyl)methylene)-2-oxoindolin-5-yl)ethanesulfonamide (Z)—N-(3-((4-(Dimethylamino)phenylamino)(phenyl)methylene)-2-oxoindolin-5-yl)ethanesulfonamide (Z)—N-(3-((4-Fluorophenylamino)(phenyl)methylene)-2-oxoindolin-5-yl)ethanesulfonamide (Z)—N-(3-((4-Chlorophenylamino)(phenyl)methylene)-2-oxoindolin-5-yl)ethanesulfonamide (Z)—N-(3-((4-Bromophenylamino)(phenyl)methylene)-2-oxoindolin-5-yl)ethanesulfonamide (Z)—N-(3-((4-Nitrophenylamino)(phenyl)methylene)-2-oxoindolin-5-yl)ethanesulfonamide (Z)—N-(3-((4-(Morpholinomethyl)phenylamino)(phenyl)methylene)-2-oxoindolin-5-yl)ethanesulfonamide N-(3-(Diphenylmethylene)-2-oxoindolin-5-yl)ethanesulfonamide (Z)—N-(2-oxo-3-(Phenyl(p-tolyl)methylene)indolin-5-yl)ethanesulfonamide (Z)—N-(3-((4-Methoxyphenyl)(phenyl)methylene)-2-oxoindolin-5-yl)ethanesulfonamide (Z)—N-(3-((4-(Dimethylamino)phenyl)(phenyl)methylene)-2-oxoindolin-5-yl)ethanesulfonamide (Z)—N-(3-((4-Fluorophenyl)(phenyl)methylene)-2-oxoindolin-5-yl)ethanesulfonamide (Z)—N-(3-((4-Chlorophenyl)(phenyl)methylene)-2-oxoindolin-5-yl)ethanesulfonamide (Z)—N-(3-((4-Bromophenyl)(phenyl)methylene)-2-oxoindolin-5-yl)ethanesulfonamide (Z)—N-(3-((4-Nitrophenyl)(phenyl)methylene)-2-oxoindolin-5-yl)ethanesulfonamide
(Z)—N-(2-oxo-3-(Phenyl(4-(piperidin-1-ylmethyl)phenyl) methylene)indolin-5-yl)ethanesulfonamide
(Z)—N-(3-((4-(Morpholinomethyl)phenyl)(phenyl)methylene)-2-oxoindolin-5 yl)ethanesulfonamide
(Z)—N-(3-Benzylidene-2-oxoindolin-5-yl)ethanesulfonamide
(Z)—N-(3-(4-Methylbenzylidene)-2-oxoindolin-5-yl)ethanesulfonamide
(Z)—N-(3-(4-Methoxybenzylidene)-2-oxoindolin-5-yl)ethanesulfonamide
(Z)—N-(3-(4-(Dimethylamino)benzylidene)-2-oxoindolin-5-yl)ethanesulfonamide
(Z)—N-(3-(4-Fluorobenzylidene)-2-oxoindolin-5-yl)ethanesulfonamide
(Z)—N-(3-(4-Chlorobenzylidene)-2-oxoindolin-5-yl)ethanesulfonamide
(Z)—N-(3-(4-Bromobenzylidene)-2-oxoindolin-5-yl)ethanesulfonamide
(Z)—N-(3-(4-Nitrobenzylidene)-2-oxoindolin-5-yl)ethanesulfonamide
(Z)—N-(2-oxo-3-(4-(Piperidin-1-ylmethyl)benzylidene)indolin-5-yl)ethanesulfonamide
(Z)—N-(3-(4-(Morpholinomethyl)benzylidene)-2-oxoindolin-5-yl)ethanesulfonamide
(Z)—N-(2-oxo-3-(Phenylimino)indolin-5-yl)ethanesulfonamide
(Z)—N-(2-oxo-3-(p-Tolylimino)indolin-5-yl)ethanesulfonamide
(Z)—N-(3-((4-Methoxyphenyl)imino)-2-oxoindolin-5-yl) ethanesulfonamide
(Z)—N-(3-((4-(Dimethylamino)phenyl)imino)-2-oxoindolin-5-yl)ethanesulfonamide
(Z)—N-(3-((4-Fluorophenyl)imino)-2-oxoindolin-5-yl)ethanesulfonamide
(Z)—N-(3-((4-Chlorophenyl)imino)-2-oxoindolin-5-yl)ethanesulfonamide
(Z)—N-(3-((4-Bromophenyl)imino)-2-oxoindolin-5-yl)ethanesulfonamide
(Z)—N-(3-((4-Nitrophenyl)imino)-2-oxoindolin-5-yl)ethanesulfonamide
(Z)—N-(2-oxo-3-((4-(Piperidin-1-ylmethyl)phenyl)imino) indolin-5-yl)ethanesulfonamide and
(Z)—N-(3-((4-(Morpholinomethyl)phenyl)imino)-2-oxoindolin-5-yl)ethanesulfonamide.

In another embodiment of the invention, in the pharmacological composition for treating the condition associated with the liver disease, the compound has a structural according to Formula I, wherein X is carbon, n is 0, $R^4$ is H, $R^5$ is H or Br, $R^6$ is H, $R^7$ is H, and the compound is a member of the group consisting of:
(Z)—N-Cyclohexyl-2-(2-oxo-3-(phenyl(phenylamino) methylene)indolin-1-yl)-2-phenylacetamide
(Z)—N-Cyclohexyl-2-(2-oxo-3-((phenylamino)methylene) indolin-1-yl)-2-phenylacetamide
(Z)-3-Benzylideneindolin-2-one
(Z)-3-(4-Fluorobenzylidene)indolin-2-one
(Z)-3-(4-Chlorobenzylidene)indolin-2-one
(Z)-3-(4-Bromobenzylidene)indolin-2-one
(Z)-3-(4-Methoxybenzylidene)indolin-2-one
(Z)-3-(4-(Dimethylamino)benzylidene)indolin-2-one
(Z)-3-Benzylidene-5-bromoindolin-2-one
(Z)-3-(Pyridin-2-ylmethylene)indolin-2-one and
(Z)-5-Bromo-3-(pyridin-2-ylmethylene)indolin-2-one.

In a different embodiment of the invention, in the pharmacological composition for treating the condition associated with the liver disease, the compound has a structural according to Formula I, wherein X is nitrogen, n is 0, $R^4$ is H, $R^5$ is H or Br, $R^6$ is H, $R^7$ is H, and the compound is a member of the group consisting of:
(Z)-3-((4-Chlorophenyl)imino)indolin-2-one
(Z)-3-((4-Bromophenyl)imino)indolin-2-one
(Z)-3-((4-Nitrophenyl)imino)indolin-2-one
(Z)-3-(p-Tolylimino)indolin-2-one
(Z)-3-(Pyridin-3-ylimino)indolin-2-one and
(Z)-3-((Furan-2-ylmethyl)imino)indolin-2-one.

In an embodiment of the invention, the compound in the pharmaceutical composition is Hesperadin, which is (Z)—N-(2-oxo-3-(Phenyl(4-(piperidin-1-ylmethyl)phenylamino) methylene)indolin-5-yl)ethanesulfonamide.

In an embodiment of the invention, the liver disease that can be treated by the pharmaceutical composition includes hepatitis due to hepatitis B virus, hepatitis due to hepatitis C virus, hepatitis due to chronic alcohol consumption, hepatitis due to metabolic disorder, hepatitis due to autoimmune disorder, hepatitis due to drug-induced injury, hepatitis due to biliary obstruction, liver fibrosis and cirrhosis.

In an embodiment of the invention, at least one collagen is inhibited by the pharmaceutical composition. The at least one collagen is a member is selected from the group consisting of collagen type I, collagen type III, collagen type IV, collagen type V, collagen type VI and collagen type VII.

In an embodiment of the invention, the compound utilized in the pharmaceutical composition is Hesperadin, and the liver disease that is treated includes hepatitis due to hepatitis B virus, hepatitis due to hepatitis C virus, hepatitis due to chronic alcohol consumption, hepatitis due to metabolic disorder, hepatitis due to autoimmune disorder, hepatitis due to drug-induced injury, hepatitis due to biliary obstruction, liver fibrosis and cirrhosis.

In an embodiment of the invention, the compound utilized in the pharmaceutical composition is Hesperadin, and the at least one collagen that is inhibited includes collagen type I, collagen type III, collagen type IV, collagen type V, collagen type VI and collagen type VII.

Hesperadin Altered HSC Morphology and Inhibited HSC Proliferation

Figure 2:
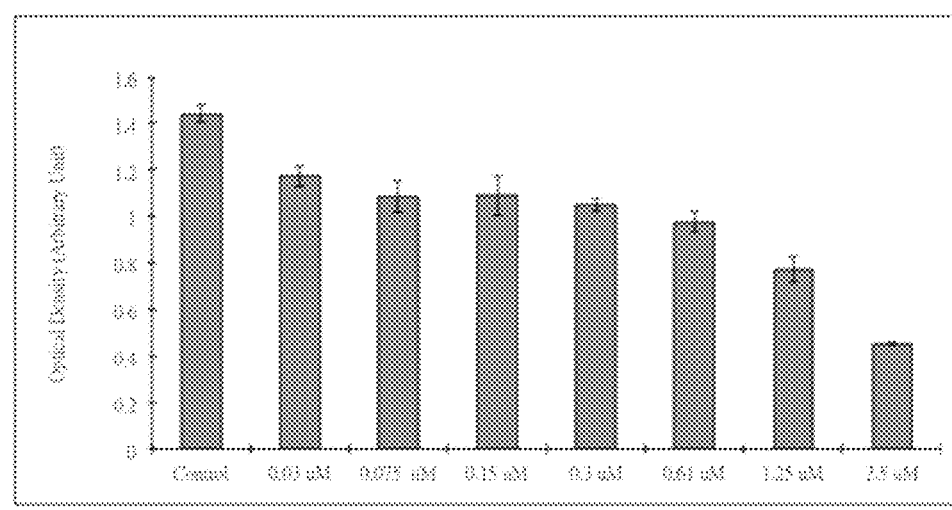
FIG. 2 is a bar chart that illustrates the effects of various concentrations of Hesperadin on the proliferation HSC's in terms of optical density. MTT analysis showed that Hesperadin suppressed HSC proliferation in a dose-dependent manner.
Figure 3:
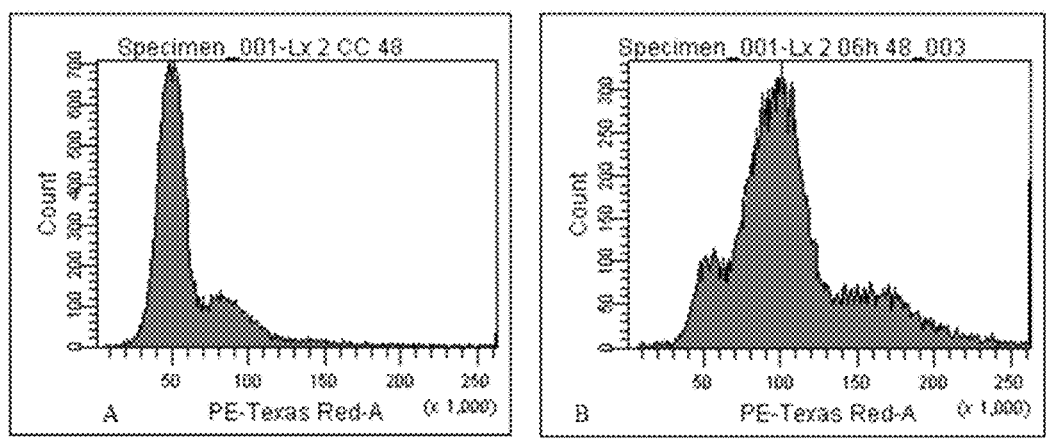
FIG. 3 is a collection of flow cytometry histograms A and B that show the effects of Hesperadin on cell cycle progression of human HSC (LX-2) cells. Histogram A is the control in which HSC cells are not treated with Hesperadin, and Histogram B represents HSC cells having been treated with Hesperadin at 0.625 µM.

Human HSCs were cultured in the presence of 0.625 or 1.25 µM of Hesperadin for 48 hrs. In the control cultures, the HSCs appeared morphologically to be like fibroblasts (FIG. 1A). In the presence of Hesperadin, the HSC cells increased in size 2-3 folds (FIGS. 1B and C). The effect of Hesperadin on HSC growth was examined. MTT analysis revealed that hesperadin inhibited HSC proliferation in a dose dependent manner (FIG. 2). The cell-cycle progression of HSCs is further analyzed in the presence of 0.625 µM Hesperadin using Flow Cytometry. It was determined that there were significantly more HSCs in the G2-M phase than those in the control cultures (FIG. 3). Hesperadin appeared to block cytokinesis.

Figure 4:
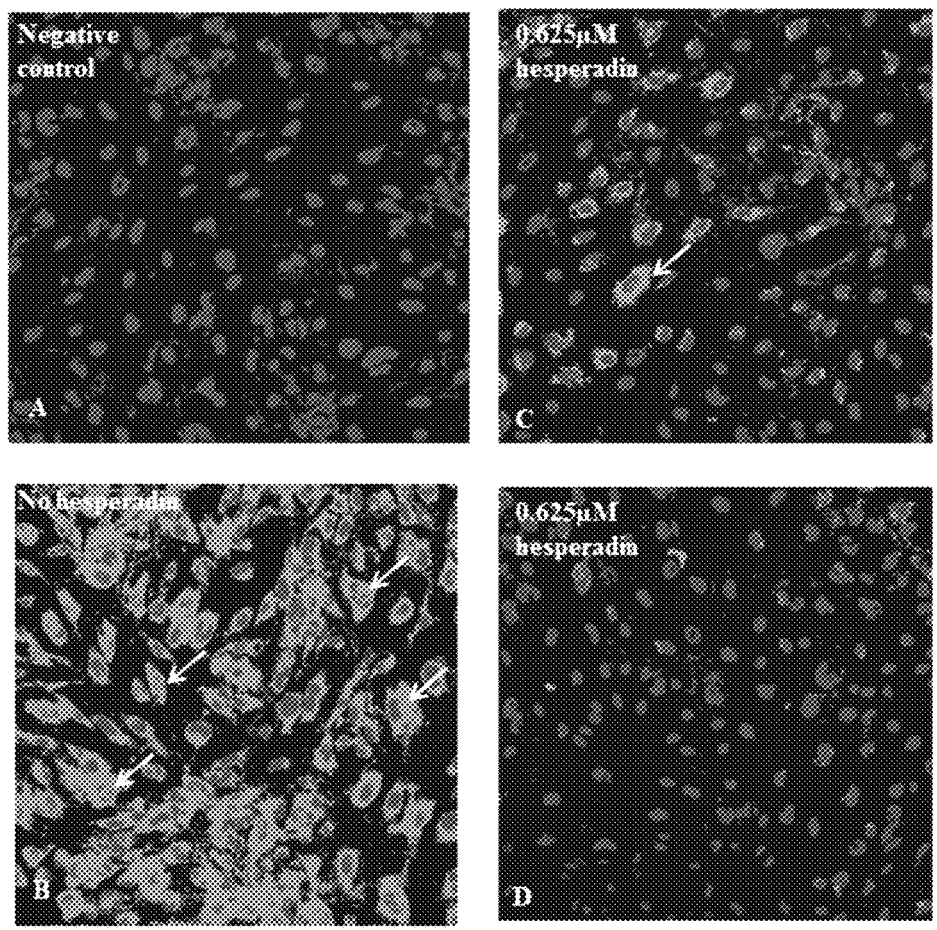
FIG. 4 is a collection of microscope images A, B, C and D of HSC cells that show the suppressive effect of Hesperadin on collagen type I expression. Image A is the negative control, with no primary antibody added. Image B shows that activated HSC's, in the absence of Hesperadin, strongly express collagen type I (white arrows), which is stained with immunofluorescent label. Images C and D represent HSC cultures that have been treated with Hesperadin at 0.625 µM for 48 hours. The diminished presence of immunofluorescent-labeled collagen type I in images C and D indicate that Hesperadin inhibits the synthesis of collagen type I.
Figure 5:
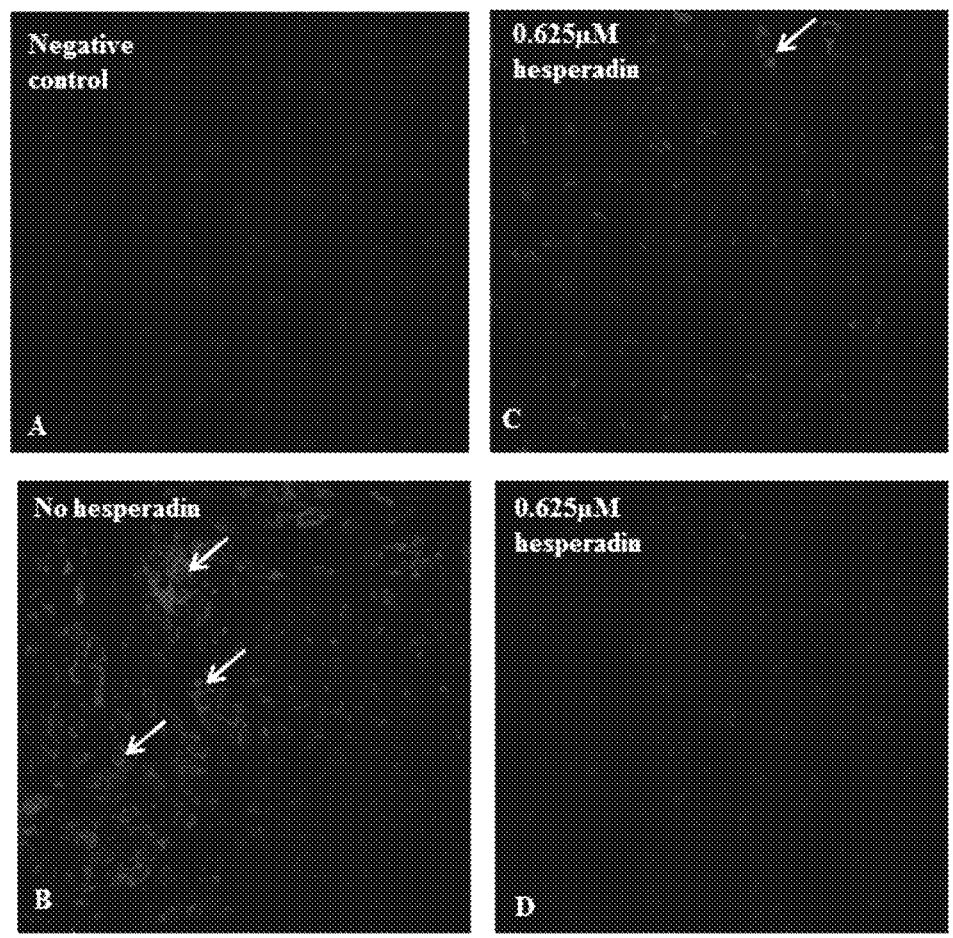
FIG. 5 is a collection of microscope images A, B, C and D of HSC cells that show the suppressive effect of Hesperadin on collagen type III expression. Image A is the negative control, with no primary antibody added. Image B shows that activated HSC's, in the absence of Hesperadin, strongly express collagen type III (white arrows), which is stained with immunofluorescent label. Images C and D represent HSC cultures that have been treated with Hesperadin at 0.625 µM for 48 hours. The diminished presence of immunofluorescent-labeled collagen type III in images C and D indicate that Hesperadin inhibits the synthesis of collagen type III.
Figure 6:
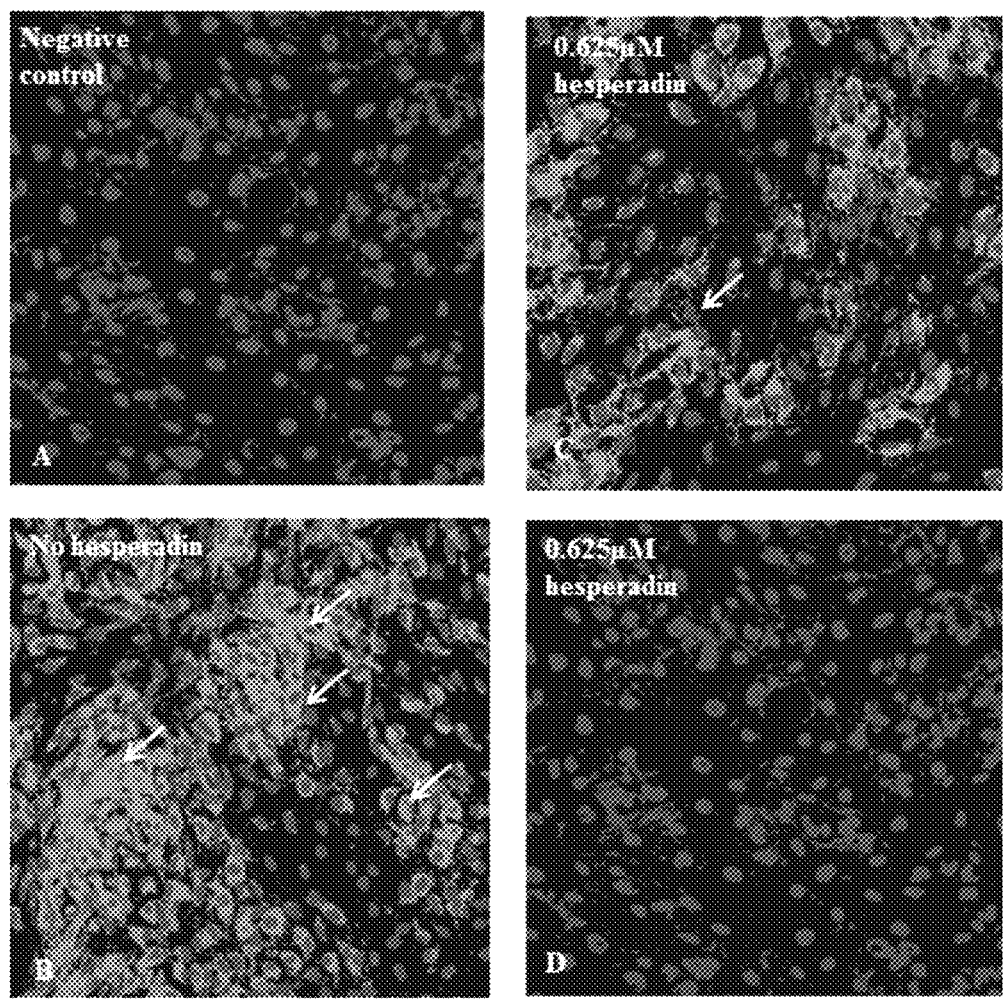
FIG. 6 is a collection of microscope images A, B, C and D of HSC cells that show the suppressive effect of Hesperadin on collagen type IV expression. Image A is the negative control, with no primary antibody added. Image B shows that activated HSC's, in the absence of Hesperadin, strongly express collagen type IV (white arrows), which is stained with immunofluorescent label. Images C and D represent HSC cultures that have been treated with Hesperadin at 0.625 µM for 48 hours. The diminished presence of immunofluorescent-labeled collagen type IV in images C and D indicate that Hesperadin inhibits the synthesis of collagen type IV.
Figure 7:
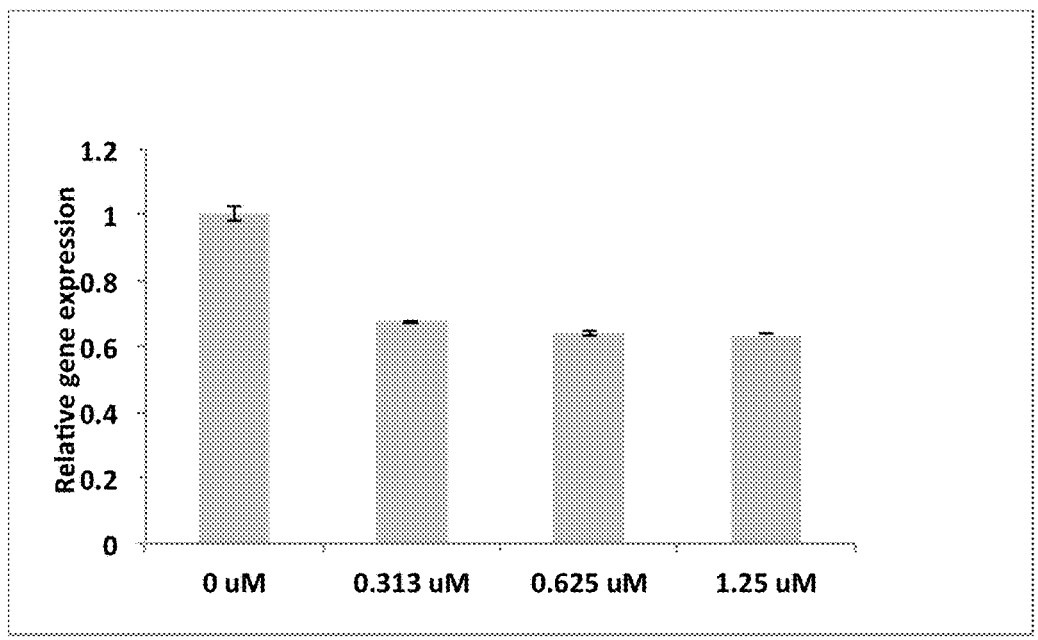
FIG. 7 is a bar chart that represents real-time RT-PCR analysis, showing the effect of Hesperadin on collagen 1A1 gene expression.
Figure 8:
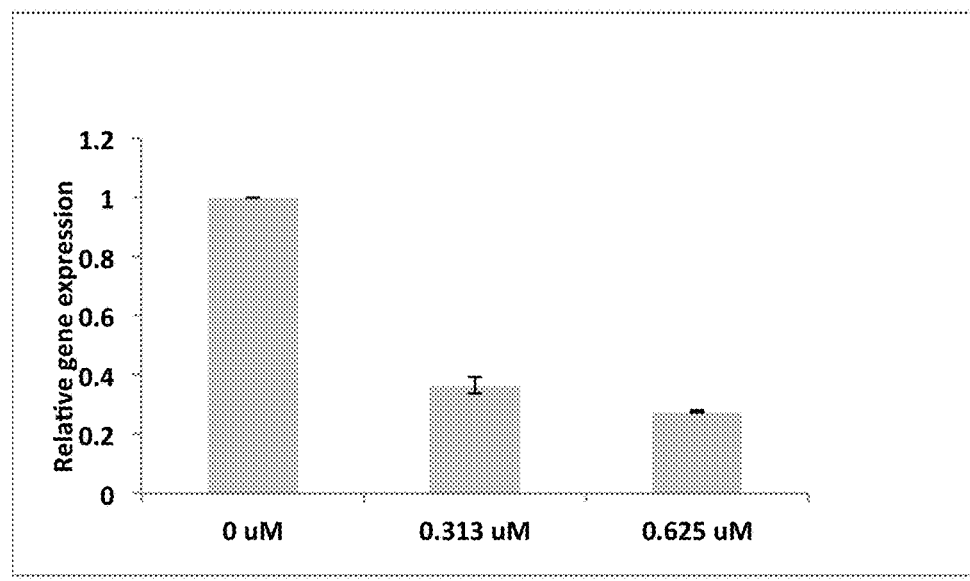
FIG. 8 is a bar chart that represents real-time RT-PCR analysis, showing the effect of Hesperadin on collagen 3A1 gene expression.
Figure 9:
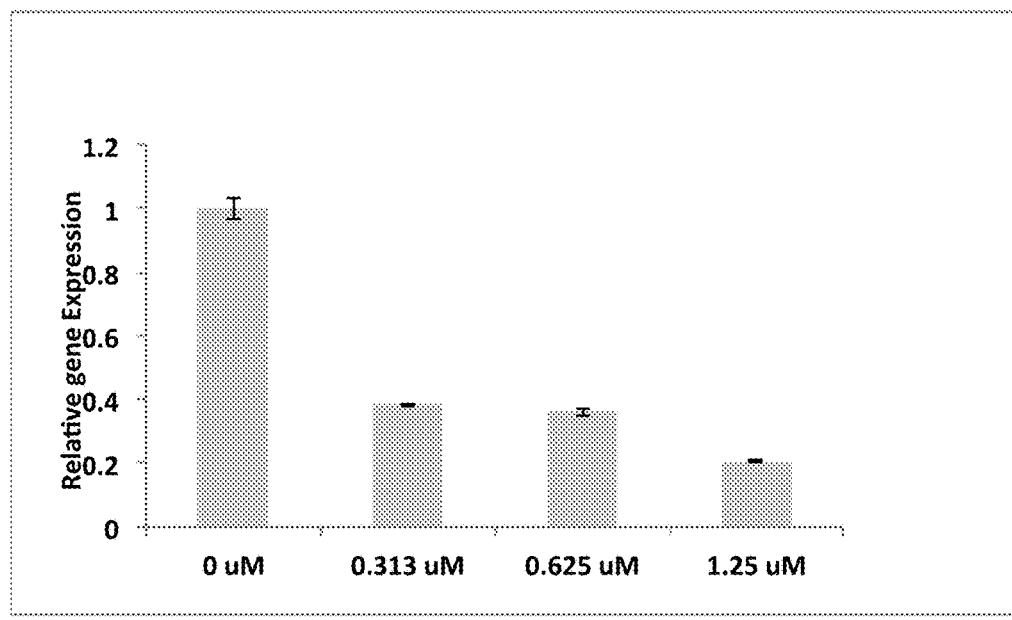
FIG. 9 is a bar chart that represents real-time RT-PCR analysis, showing the effect of Hesperadin on MMP-2 gene expression.
Figure 10:
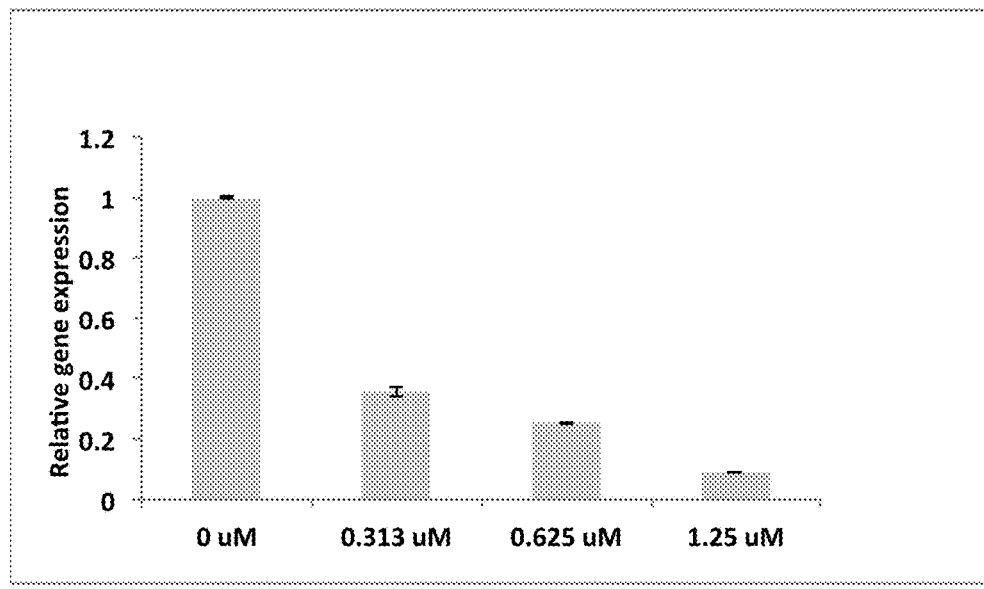
FIG. 10 is a bar chart that represents real-time RT-PCR analysis, showing the effect of Hesperadin on MMP-9 gene expression.
Figure 11:
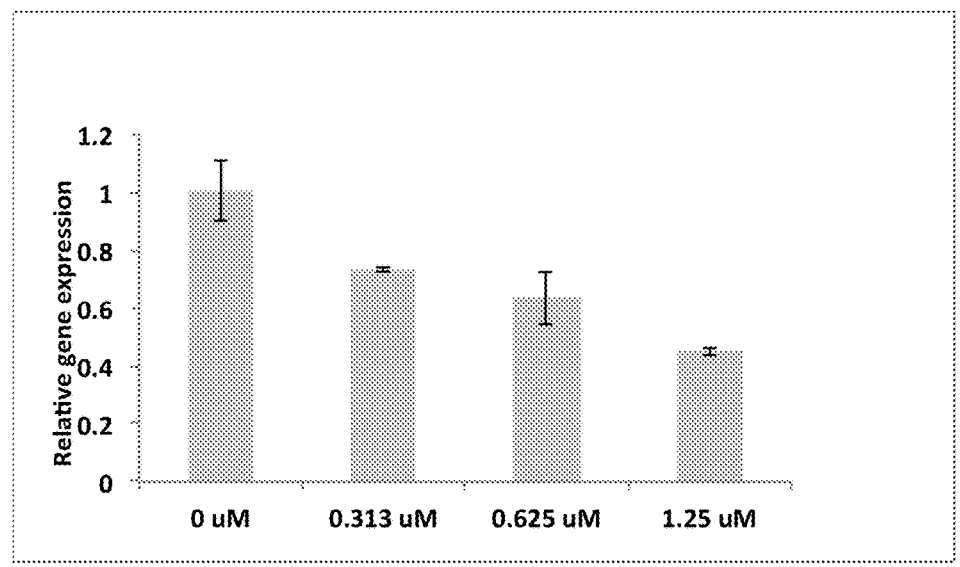
FIG. 11 is a bar chart that represents real-time RT-PCR analysis showing the effect of Hesperadin on TIMP-1 gene expression.

Hesperadin Suppressed Collagens, Matrix Metalloproteinase (MMP) and Tissue Inhibitor of Metalloproteinase (TIMP) Gene and Protein Expression by Human HSCs The effect of Hesperadin on the expression of various extracellular matrix associated genes and proteins by activated HSCs in culture was investigated. The HSCs were treated with 0.625 µM of Hesperadin for 24-48 hours and processed for immunofluorescent staining Confocal microscopic analysis revealed that collagen type I and collagen type III were normally expressed by activated human HSC. However, when the cultures were treated with Hesperadin, this small molecule significantly inhibited both collagens type-I (FIG. 4), type-III (FIG. 5) and type-IV expressions (FIG. 6). This observation was confirmed by real-time RT-PCR analysis on mRNA expression (Collagen 1A1 in FIG. 7 and Collagen 3A1 in FIG. 8). The ability of Hesperadin to affect MMPs and TIMPs expression were determined since these genes are normally involved in regulating ECM homeostasis in tissues. Real-time RT-PCR revealed that hesperadin inhibited MMP-2 (FIG. 9), MMP-9 (FIG. 10) and TIMP-1 (FIG. 11) mRNA expression.

Hesperadin Inhibited Liver Fibrosis In Vivo

Figure 12:
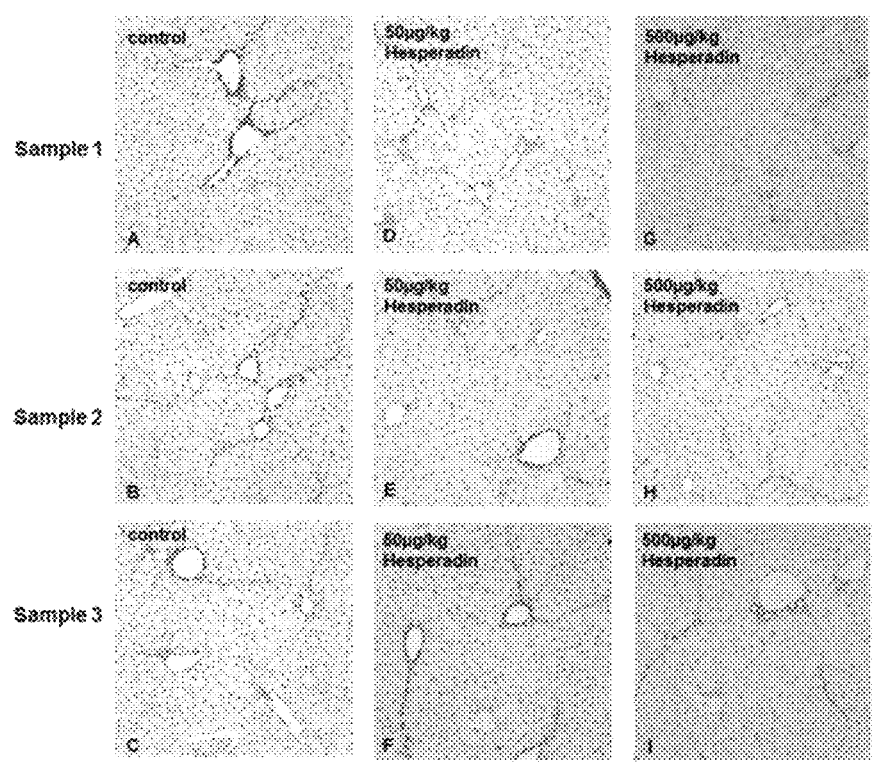
FIG. 12 is a collection of microscope images A, B, C, D, E, F, G, H and I, showing inhibition of liver fibrosis in vivo by Hesperadin in mice. Representative immunohistological staining for collagen type I, from 3 different liver samples. Control mice were injected with DMSO (images A, B and C) twice a week for 15 days, following 6 weeks of $CCl_4$ treatment. Collagen type I are found distributed in the peripherally of the hepatic lobules, the portal areas, the lining of the sinusoid and around the central veins. The mice were also treated with Hesperadin at 50 μg/kg (images D, E and F) or at 500 μg/kg (images G, H and I). It can be observed that there is significantly less collagen staining in the liver of mice that has been treated with 500 μg/kg Hesperadin. The number of mice in each group is 5.
Figure 13:
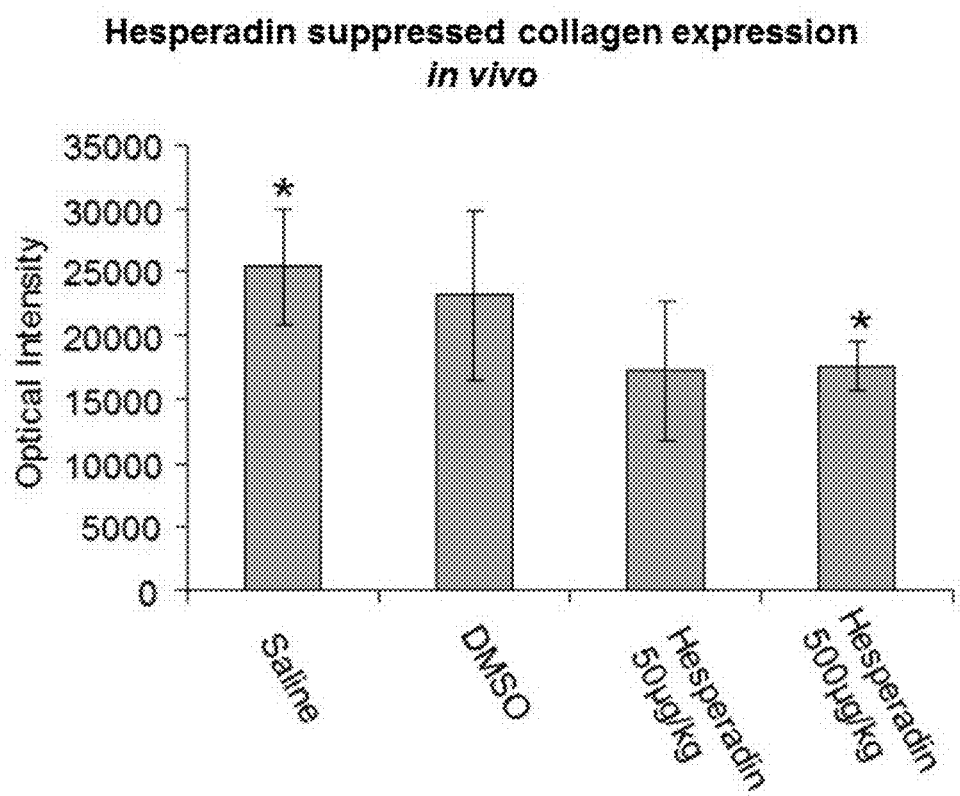
FIG. 13 is a bar chart showing quantitation of the immunohistological staining for collagen type I in liver sections of saline, DMSO and Hesperadin treated fibrotic mice. Measurement of the intensity of the collagen staining of the different groups confirmed that at 500 μg/kg of Hesperadin, there was a significant reduction in collagen type I production and expression ($p<0.05$).

The ability of Hesperadin to inhibit collagen expressions in a liver fibrosis mouse model was then examined. To induce fibrosis in the liver, mice were injected with carbon tetrachloride, twice a week, for 6 weeks. In control group of mice, they were injected with DMSO/saline, twice a week for 2 weeks. For the experimental group of mice, they were injected with either 50 or 500 µg/kg Hesperadin after chronic carbon tetrachloride treatment. The liver from the control and experimental groups of mice were harvested and processed for immunohistological staining Examination of the histological sections revealed that normally, collagen type I is only weakly expressed in the liver. In contrast, following chronic carbon tetrachloride treatment, collagen type I was expressed strongly at the lobules, the portal areas, the lining of the sinusoid and around the central veins (FIGS. 12A and 12B). However, in both 50 and 500 µg/kg Hesperadin treated carbon tetrachloride-induced fibrotic livers, there were less collagen type I evident in the histological sections—especially around the liver portal regions (FIGS. 12C and 12D, respectively). The intensity of the collagen staining was quantified and confirmed at 500 µg/kg Hesperadin, there was a significant reduction in collagen type I expression (FIG. 13, $p<0.05$). In mice of carbon tetrachloride treatment alone, collagen type I was strongly expressed in the periphery of the hepatic sinusoids.

Vitamin A-Coated Liposome Encapsulated with Hesperadin to Target Hepatic Stellate Cells In Vivo The drug can be further formulated by linking to liposomes coated with vitamin-A, which can target the HSC cells directly, since HSC cells are normally the storage sites for vitamin-A (61). The ratio of Hesperadin:vitamin A:liposome is shown in Table 1.

TABLE 1

Ratio of Hesperadin/vitamin-A/liposome

| Reagents | Ingredients |
|---|---|
| Liposome | Anionic empty lipid powder (Coatsome EL-01-A):DPPC:cholesterol:DPPG (3:4:3 mixture) |
| Vitamin A | Vitamin A: liposome (2:1 ratio mixture) |
| Hesperadin | Hesperadin (2-50 µM)/vitamin A/liposome mixed-reagent |

EXAMPLES

The following examples are set forth so as to provide those of ordinary skills in the art with a complete disclosure and description of how to make and use the present invention, and are not intended to limit the scope of what the inventors regard as their invention nor are they intended to represent that the experiments below are all or the only experiments performed.

Example 1

Small molecule Hesperadin [CAS 422513-13-1] was purchased from Selleckchem Lab (Houston, Tex., USA). A stock solution of 10 mM was prepared in dimethyl sulfoxide (DMSO). In this embodiment, compounds were prepared according to condensation reaction of 2-indolinone (oxindole) or substituted 2-indolinone with aldehydes in the presence of base as described in those examples. 2-Indolinone is commercially available, whereas 5-bromoindolin-2-one is prepared from halogenation using N-bromosuccinimide (NBS). The corresponding Schiff base analogs were prepared from condensation of aryl and alkyl amine with commercially available isatin. Using palladium-catalyzed reaction of Ugi adduct with aniline derivatives, the target N-alkylated 3-(anilinoarylmethylene)-2-oxindoles were prepared for further investigation of the corresponding structure-activity relationships.

Example 2

A. Isolation and Culture of Rodent Hepatic Stellate Cells (HSC)

HSC cells were isolated and purified from freshly harvested rat liver to establish functionally intact HSC according to methods described previously (62,63). Briefly, HSCs were isolated from livers of adult female SD rats (125-200 g) by in situ perfusion with pronase and collagenase. Crude cell suspensions were purified to >95% homogeneity by centrifugation over a discontinuous gradient of Accudenz (Accurate Scientific). The cells were suspended in DMEM with 10% FCS (GIBCO BRL) and plated on uncoated tissue culture plastic dishes at a density of $1.5 \times 10^5$ cells/cm$^2$. After 2 days, cell debris and non-adherent cells were removed by washing and the medium was changed every 2-3 days thereafter. The purity of the cultures was assessed by microscopy, examining for intrinsic vitamin A auto-fluorescence and by immunocytochemistry using monoclonal antibodies against alpha-smooth muscle antigen ($\alpha$-SMA) and desmin. Cell viability was examined by Trypan blue exclusion staining HSC are normally rounded and quiescent when plated onto culture dishes. However after approximately 10 days in culture, they were activated and becoming very flatten and took on a star-like appearance. These cells were expressing $\alpha$-SMA and desmin biomarkers, proliferating excessively and transdifferentiated into a highly contractile cell type, called myofibroblasts.

B. Preparation of Derivatives by Chemical Synthesis

Example a: (Z)—N-Cyclohexyl-2-(2-oxo-3-(phenyl (phenylamino)methylene)indolin-1-yl)-2-phenylacetamide

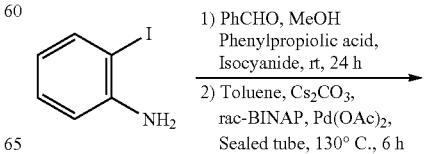

1) PhCHO, MeOH
   Phenylpropiolic acid,
   Isocyanide, rt, 24 h
2) Toluene, Cs$_2$CO$_3$,
   rac-BINAP, Pd(OAc)$_2$,
   Sealed tube, 130° C., 6 h

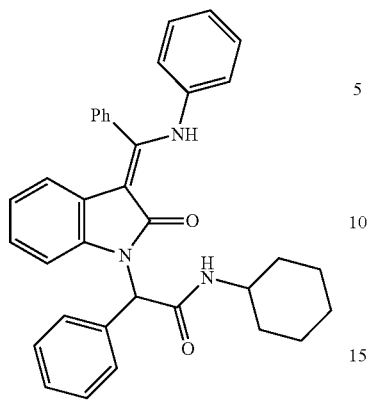

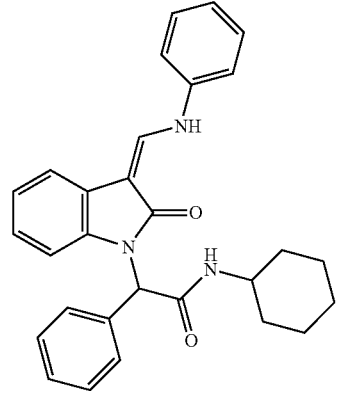

A solution of 2-Iodoaniline (219 mg, 1 mmol) and benzaldehyde (101 μL, 1 mmol) in MeOH (5 mL) was stirred for 30 min. Then, phenyl propiolic acid (146 μL, 1 mmol) and isocyanide (124 μL, 1 mmol) were added and the mixture was stirred for 24 h. Upon the complete of reaction monitored by thin layer chromatography (TLC), the mixture was washed with saturated NaHCO$_3$ (30 mL) and was extracted with ethyl acetate (20 mL×3). The combined organic extract was dried with Na$_2$SO$_4$. Concentration followed by column chromatography (Hexane:dichloromethane (DCM) 2:1 to DCM) gave the product phenylpropiolamide in 76% yield as off-white precipitate.

A solution of phenylpropiolamide (80 mg, 0.14 mmol), aniline (26 μL, 0.29 mmol), rac-BINAP (9.1 mg, 14.6 μmol), palladium acetate (2.2 mg, 9.8 μmol), caesium carbonate (92.5 mg, 0.28 mmol) in toluene (5 mL) was degassed using freeze-pump-thaw. The solution was stirred at 130° C. for 6 hours. After the solution was cooled to room temperature, the crude product was purified by column chromatography (dichloromethane/diethyl ether, 80:1 to 5:1, v/v) to yield the corresponding indolinone in 70% yield as yellow precipitate; $^1$H NMR (400 MHz, CDCl$_3$) δ 1.14-2.04 (10H, m), 3.92-3.93 (1H, m), 6.00 (1H, d, J=7.8 Hz), 6.32 (1H, brs), 6.51 (1H, m), 6.63-6.67 (1H, m), 6.77 (2H, d, J=7.9 Hz), 6.88-6.95 (2H, m), 6.99 (1H, t, J=7.0 Hz), 7.11 (2H, t, J=7.7 Hz), 7.28-7.56 (10H, m), 11.91 (1H, brs); MS (EI) m/z (relative intensity) 527 (M$^+$, 46%).

Example b: (Z)—N-Cyclohexyl-2-(2-oxo-3-((phenylamino)methylene)indolin-1-yl)-2-phenylacetamide

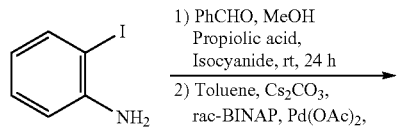

1) PhCHO, MeOH
   Propiolic acid,
   Isocyanide, rt, 24 h
2) Toluene, Cs$_2$CO$_3$,
   rac-BINAP, Pd(OAc)$_2$,
   Sealed tube, 130° C., 6 h A solution of 2-iodoaniline (658 mg, 3 mmol) and benzaldehyde (304 μL, 3 mmol) in MeOH (11 mL) was stirred for 30 min. Then, propiolic acid (186 μL, 3 mmol) and isocyanide (373 μL, 3 mmol) were added and the mixture was stirred for 24 h. Upon the complete of reaction monitored by TLC (dichloromethane, R$_f$=0.23), the mixture was washed with saturated NaHCO$_3$ (30 mL) and was extracted with dichloromethane (20 mL×3). The combined organic extract was dried with Na$_2$SO$_4$. Concentration followed by recrystallization (dichloromethane:hexane) gave the product propiolamide in 82% yield as off-white precipitate.

A solution of propiolamide (101 mg, 0.21 mmol), aniline (38 μL, 0.42 mmol), rac-BINAP (12.8 mg, 20.6 μmol), palladium acetate (2.3 mg, 10.2 μmol), caesium carbonate (135 mg, 0.41 mmol) in acetonitrile (5 mL) was degassed using freeze-pump-thaw. The solution was stirred at 130° C. for 6 hours. After the solution was cooled to room temperature, the crude product was purified by column chromatography (dichloromethane/diethyl ether, 50:1 to 15:1, v/v) to yield the corresponding indolinone in 21% yield as yellow precipitate.

Example c: (Z)-3-Benzylideneindolin-2-one

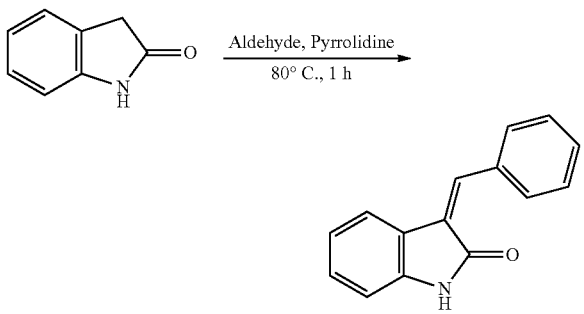

A solution of 2-oxindole (269 mg, 2 mmol), benzaldehyde (203 μL, 2 mmol) and pyrrolidine (181 μL, 4 mmol) in ethanol (2 mL) was heated at 80° C. for 1 h. The reaction mixture was cooled down to 4° C. and the orange precipitate was filtered and washed with hexane (3 mL×3). The product was further recrystallized from dichloromethane and hexane to receive the title product in 82% yield; $^1$H NMR (400 MHz, CDCl$_3$) δ 6.85-6.93 (2H, m), 7.20-7.25 (1H, m), 7.44-7.50 (3H, m), 7.63-7.68 (3H, m), 7.85 (1H, s), 8.63 (1H brs); MS (EI) m/z (relative intensity) 221 (M$^+$, 100%).

Example d:
(Z)-3-(4-Fluorobenzylidene)indolin-2-one

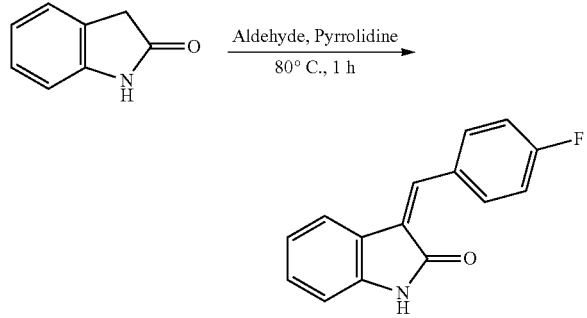

The title compound was prepared in analogy to Example c to give orange powder in 71% yield.

Example e:
(Z)-3-(4-Chlorobenzylidene)indolin-2-one

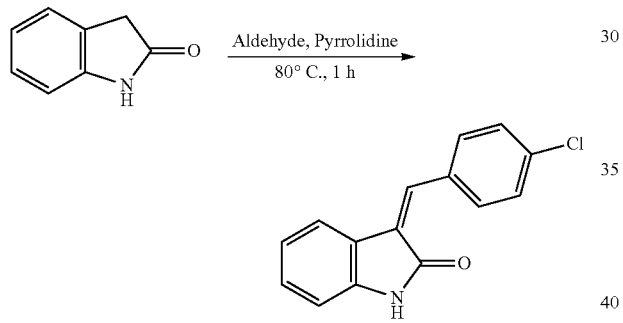

The title compound was prepared in analogy to Example c to give orange powder in 78% yield.

Example f:
(Z)-3-(4-Bromobenzylidene)indolin-2-one

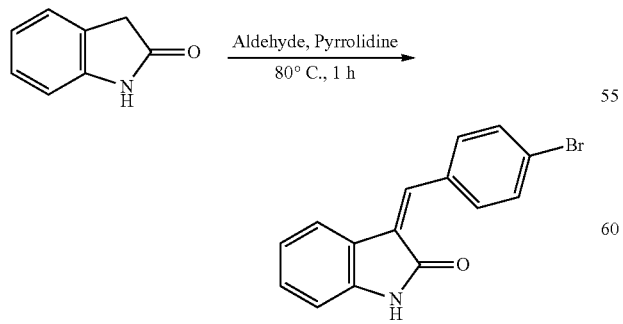

The title compound was prepared in analogy to Example c to give orange powder in 79% yield.

Example g:
(Z)-3-(4-Methoxybenzylidene)indolin-2-one

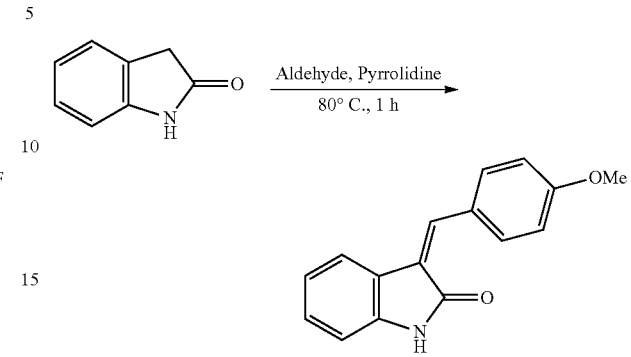

The title compound was prepared in analogy to Example c to give orange powder in 84% yield.

Example h: (Z)-3-(4-(Dimethylamino)benzylidene)indolin-2-one

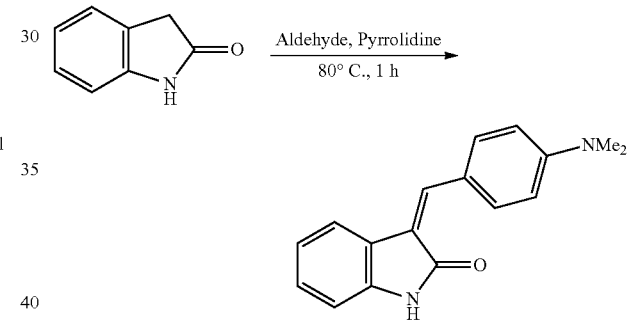

The title compound was prepared in analogy to Example c to give orange powder in 50% yield.

Example i:
(Z)-3-Benzylidene-5-bromoindolin-2-one

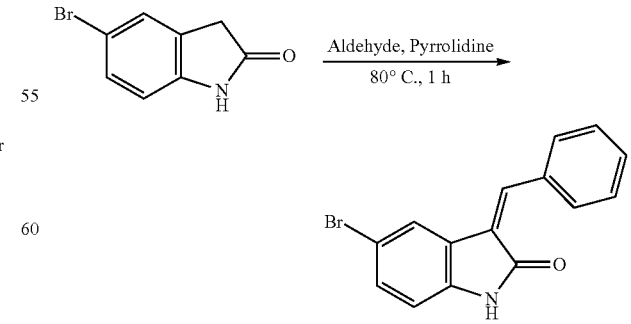

The title compound was prepared in analogy to Example c to give orange powder in 71% yield.

Example j: (Z)-3-(Pyridin-2-ylmethylene)indolin-2-one

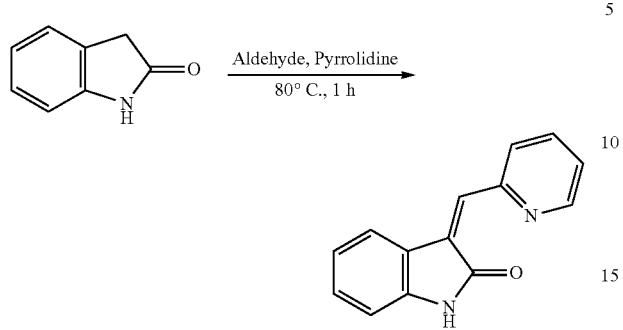

The title compound was prepared in analogy to Example c to give orange powder in 51% yield.

Example k: (Z)-5-Bromo-3-(pyridin-2-ylmethylene)indolin-2-one

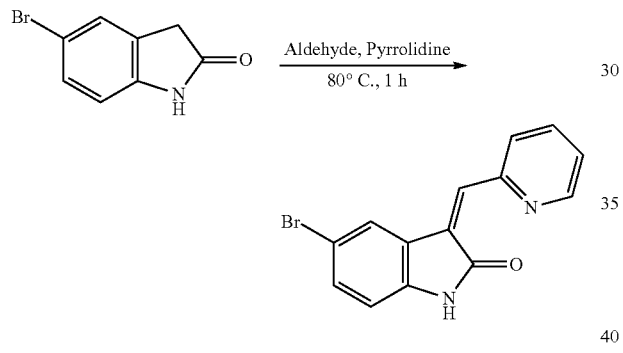

The title compound was prepared in analogy to Example c to give orange powder in 80% yield.

Example l: (Z)-3-((4-Chlorophenyl)imino)indolin-2-one

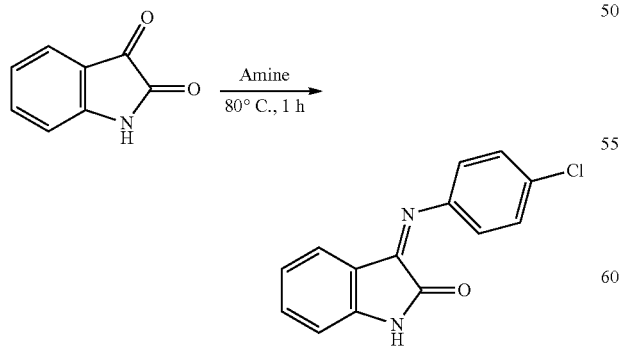

In the absence of pyrrolidine, the title compound was prepared in analogy to Example c to give orange powder in 95% yield.

Example m: (Z)-3-((4-Bromophenyl)imino)indolin-2-one

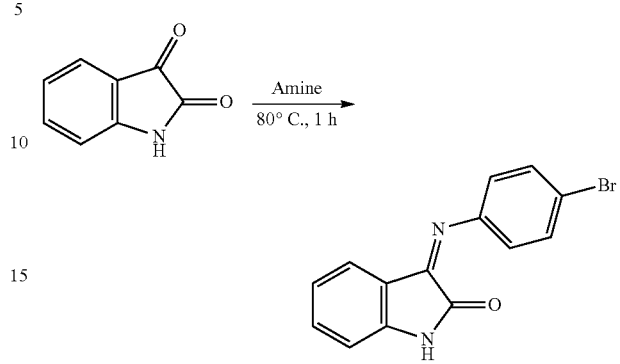

In the absence of pyrrolidine, the title compound was prepared in analogy to Example c to give orange powder in 70% yield.

Example n: (Z)-3-((4-Nitrophenyl)imino)indolin-2-one

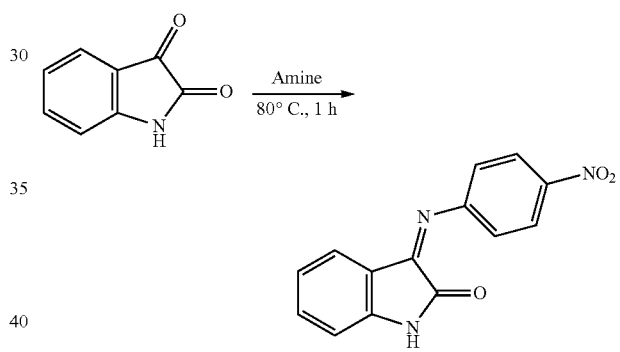

In the absence of pyrrolidine, the title compound was prepared in analogy to Example c to give orange powder in 30% yield.

Example o: (Z)-3-(p-Tolylimino)indolin-2-one

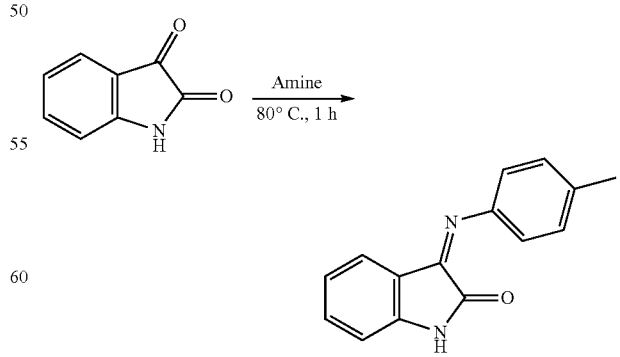

In the absence of pyrrolidine, the title compound was prepared in analogy to Example c to give orange powder in 77% yield.

Example p: (Z)-3-(Pyridin-3-ylimino)indolin-2-one

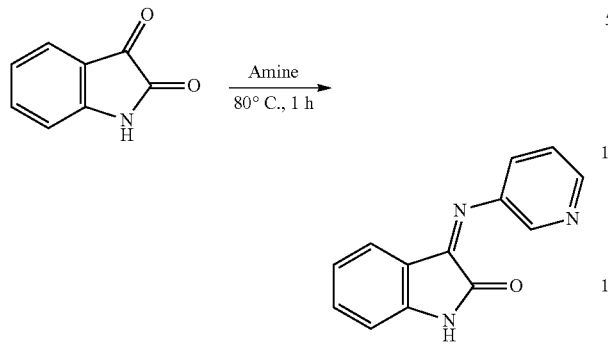

In the absence of pyrrolidine, the title compound was prepared in analogy to Example c to give orange powder in 17% yield.

Example q: (Z)-3-((Furan-2-ylmethyl)imino)indolin-2-one

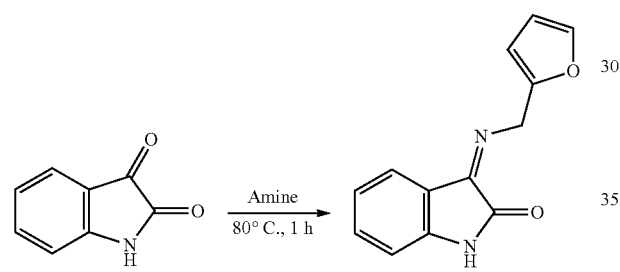

In the absence of pyrrolidine, the title compound was prepared in analogy to Example c to give orange powder in 67% yield.

Example 3

Human HSC Cell Culture, Cell Proliferation and Cell Cycle Analysis

Human Hepatic Stellate cells (LX-2 cell line) (HSCs) were obtained from the Key Lab of Regenerative Medicine, Jinan University, Guangzhou, China, which were maintained in Dulbecco's Modified Eagle Medium (DMEM)+ 10% fetal calf serum and penicillin-streptomycin (100 unit/ml and 0.1 mg/ml, respectively), in 5% $CO_2$ at 37° C. inside a humidified cell incubator. The culture medium was changed every three days. To test the effects of small molecule Hesperadin on the mouse and human HSCs, the cultures were treated with 0.625 µM of Hesperadin for 48 hrs. The cultures were then fixed in ice cold 70% ethanol and incubated in phosphate buffered saline with RNase (0.25 mg/ml), Propidium iodide dye (40 µg/ml) and 0.1% Triton X for an hour at room temperature. For cell cycle analysis, the Propidium iodide stained cells were examined using a flow cytometer ("BD LSRFortessa Cell Analyzer"). The proliferation of HSCs was also evaluated by the MTT staining assay with 3-(4,5-Dimethylthiazol-2-yl)-2,5-diphenyltetrazolium bromide). HSCs were plated at $1 \times 10^4$ cells/ml and culture overnight. Hesperadin (in serial dilutions) was then added into the culture medium for 48 hours. This was followed by addition of MTT (250 µg/ml) for a further 4 hours. The medium was eluted and the formazan crystal was dissolved in 100 µL of DMSO. The absorbance (at 570 nm) was measured using a BIORAD 3550 Microplate Reader. For experimentation, 0.625 µM of Hesperadin were added to the activated HSC culture for 24 hours and then changed to DMEM+10% FCS. In the pilot study, we had already established that 24 hours of exposure to our Hesperadin was sufficient to affect the activated HSC. The cultures were harvested for immunofluorescence and RT-PCR analysis at 24-48 hours after treatment.

Example 4

Generation of Liver Fibrosis Model in Mice

Forty female ICR mice (6 weeks old) were acquired from the MOE Key laboratory for Regenerative Medicine. To induce liver fibrosis, the mice were injected i.p. with carbon tetrachloride (1.65 ml/kg body weight suspended in 0.1 ml olive oil) twice per week for a total of 6 weeks. In the control group, mice received carbon tetrachloride injection for 6 weeks followed by DMSO or saline injections, twice a week, for two weeks. In the experimental group, mice received carbon tetrachloride for 6 weeks followed by i.p. injections of 50 µg/kg or 500 µg/kg Hesperadin, twice a week, for two weeks. At the end of experimentation, the mice were sacrificed by cervical dislocation and the liver and other organs were removed and fixed in 10% buffered formalin.

Example 5

Histology and Immunohistochemistry (IHC)

Liver samples were harvested from experimental mice or rats: (1) after 8 weeks of carbon tetrachloride or olive oil treatments and (2) 8 weeks of carbon tetrachloride treatment and 1-60 days after VA/lip/Hesperadin or VA/lip/DMSO (control) treatments. The liver samples were embedded in wax, sectioned and then stained with trichrome stain. The extent of fibrosis was scored according to Zhou, et al. (5): 1=thickened perivenular collagen and a few thin collagen septa; 2=thin septa with incomplete bridging between portal regions; 3=thin septa and extensive bridging; 4=thickened septa with complete bridging of portal regions and a nodular appearance. Collagen content was measured with a Universal Imaging (Chester, Pa.) analysis system. Briefly, trichrome-stained liver sections were analysed using an Axioskope 50 microscope (CarlZeiss Lab). An intensely labeled point was chosen to set the range of color detection for the blue trichrome stain. Collagen accumulation was calculated as the percentage of the total field at ×40 magnifications that was stained blue. The arrangement and morphology of the hepatocytes will also be examined and recorded. The wax liver sections were stained with monoclonal anti-collagen Type I, III and IV (Abcam Lab, Cambridge, UK). Briefly, the hydrated liver sections were first incubated in 3% hydrogen peroxide for 10 min to block the endogenous peroxidase activity. Primary antibodies (1:50-300 dilutions in PBS) were then applied to the sections at room temperature for 1-2 hours. Then the sections were reacted with the appropriate secondary antibody (Jackson Immuno-Research), or with the appropriate biotinylated secondary antibody and avidin. The slides were reacted with DAB as the chromogen, and counterstained with hematoxylin.

Example 6

Immunofluorescent Staining of the HSC Cultures

The circular 12 mm cover-slips, on which hepatic stellate cells were grown, were fixed with 10% formalin in PBS. The specimens were processed for immunofluorescent staining. The specimens were first treated with 1% donkey serum in PBST (0.1% Triton X in PBS) to prevent non-specific binding. They were then incubated with primary anti-human Collagen type I, type III and type IV antibodies (Abcam Lab, UK) overnight (1:100 dilution in 1% BSA with PBS). The specimens were then washed with PBST three times and incubated with donkey anti-rabbit Cys-3-conjugated antibody, or donkey anti-mouse Cys-3-conjugated antibody (1:300 dilution, Jackson ImmunoResearch). After washing, the sections were viewed and recorded using a FluoView FV1000 Confocal microscope and/or a Nikon i80 microscope respectively to identify the presence of HSC expressing collagens. The positive staining of Collagen types I, III and IV was analyzed with the Metamorph software.

Example 7

Biochemical Analysis

The blood samples harvested from control and experimental mice or rats were processed for ALT and SGOT analysis, and for biomarkers for liver dysfunction, according to methods we previously described in Lee et al., 2002 (25). The results indicated whether our Hesperadin could improve liver function through its ability to inhibit liver fibrosis Liver fibrosis was examined by using the FibroTest for markers ApopA1, haptoglobin, alpha2-macroglobulin, gamma-GT, and bilirubin according to the methods described by Koda, et al. (9).

Example 8

Statistical Analysis

Data were analyzed by one-way ANOVA or two-way ANOVA for repeated measures where appropriate, with P<0.05 as the level of significance. All data were presented as means±SE of at least 4-10 observations/group. Continuous data was expressed as mean±SD. Two tailed Student's t-test was used where appropriated, p-value<0.05 was considered statically significant.

Example 9

Real-Time RT-PCR

Collagen type-I, -III and -VI, MMP-2, MMP-9 and TIMP-1 gene expression was determined using quantitative real-time PCR. Total RNAs was isolated from the cell cultures and liver samples harvested after competition of experiments using TRIzol reagent. For cDNA synthesis, a Fermatas Revert-Aid First Strand cDNA synthesis kit was used, according to methods described by the manufacturer. Quantitation of mRNA levels was performed using a SYBR® Premix Ex Taq™ Kit (Takara) in an Applied Biosystems 7900HT Fast Real-Time PCR System. To quantify the amount of specific mRNA in the samples, a standard curve was generated for each PCR run using four amounts of the cDNA synthesized from our HSC cultures and liver samples. In each duplicate sample reaction (20 µl) 80 ng of cDNA was added, the mean was used for analysis. The PCR reaction was: Initial denaturation at 95 degree for 30 Seconds, then PCR denaturation at 95 degree, for 5 seconds, annealing at 60 degree for 30 Seconds, and polymerization at 72 degree for 60 seconds, which was repeated 40 times. Final extension was: 95 C for 15 seconds, 60 C for 60 Seconds, 72 C for 5 min and 95 C for 15 seconds. The relative expression level of each gene of interest was normalized by dividing its mRNA by that of β-actin as an endogenous control in each sample. Data was analyzed using a StatView software (Abacus Concepts Inc) with Student's t-test.

Example 10

Primer Sequences Used for Real-Time RT-PCR Analysis

```
Real Time COL1A1
                                    (SEQ. ID No. 1)
Right primer sequence: ACACGTCTCGGTCATGGTA (SEQ. ID No. 2)
Left primer sequence: AGAGGAAGGCCAAGTCGAG Real Time COL3A1
                                    (SEQ. ID No. 3)
Right primer sequence: GGACTGACCAAGATGGGAA (SEQ. ID No. 4)
Left primer sequence: GGGGAGCTGGCTACTTCTC Real Time MMP2
                                    (SEQ. ID No. 5)
Right primer sequence: GAAAGCCAGGATCCATTTT (SEQ. ID No. 6)
Left primer sequence: TGCCGCCTTTAACTGGAG Real Time MMP9
                                    (SEQ. ID No. 7)
Right primer sequence: TGGTCCACCTGGTTCAACT (SEQ. ID No. 8)
Left primer sequence: CGACGTCTTCCAGTACCGA Real Time TIMP1
                                    (SEQ. ID No. 9)
Right primer sequence: ACTTGGCCCTGATGACGAG (SEQ. ID No. 10)
Left primer sequence: CTGTTGTTGCTGTGGCTGAT
```

Example 11

Vitamin A-Coated Liposome Encapsulated with Hesperadin to Target Hepatic Stellate Cells In Vivo The efficacy of Hesperadin in fibrotic liver will be increased by using liposomal technologies to specifically target and deliver Hesperadin into hepatic stellate cells in vivo. Liposomes coated with vitamin A to embed our Hesperadin (61). The formulation of Vitamin A linked liposome coated hesperadin is shown in Table 1. Vitamin A is used in this instance as bait because the hepatic stellate cells in the liver normally function by absorbing vitamin A from the blood and storing it. In this manner Hesperadin is specifically target into activated hepatic stellate cells and inhibiting them from over-production collagen. It is also be able to reduce the optimal concentration of Hesperadin required for it to be effective (i.e. compared with Hesperadin directly injected into the blood) and increase its efficacy.

Example 12

Figure 14A:
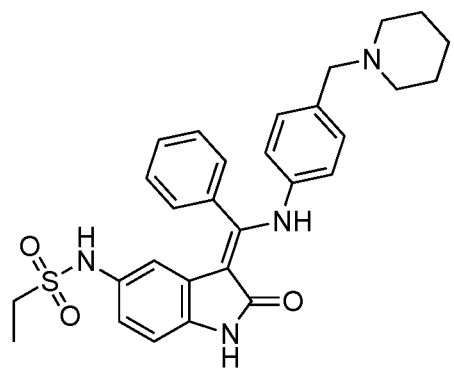
FIG. 14A shows the cell death assay (MTT assay) of (Z)—N-(2-oxo-3-(phenyl(4-(piperidin-1-ylmethyl)phenylamino)methylene)indolin-5-yl)ethanesulfonamide (Hesperadin) with human liver stellate cells in a graph having percentage of inhibition versus concentration.
Figure 14A:
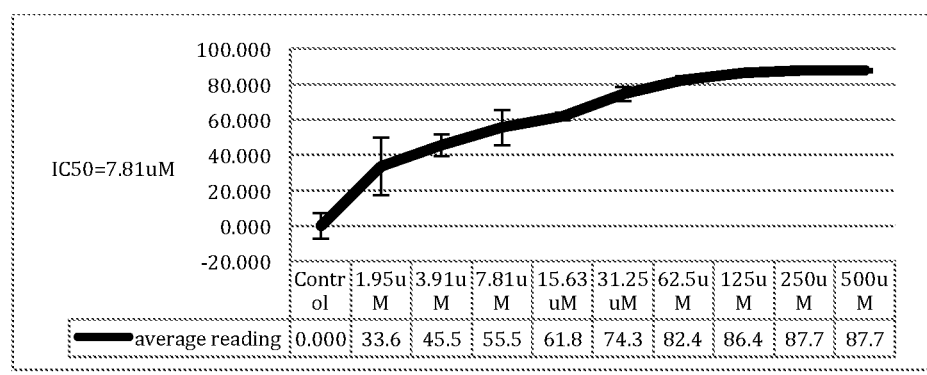
Figure 14B:
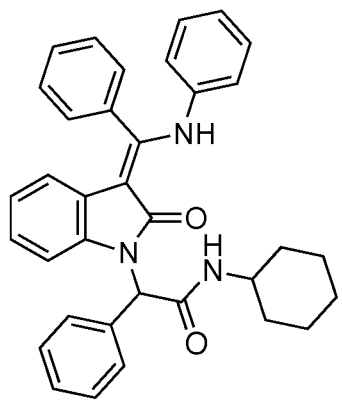
FIG. 14B shows the cell death assay (MTT assay) of (Z)—N-cyclohexyl-2-(2-oxo-3-(phenyl(phenylamino)methylene)indolin-1-yl)-2-phenylacetamide with human liver stellate cells in a graph having percentage of inhibition versus concentration.
Figure 14B:
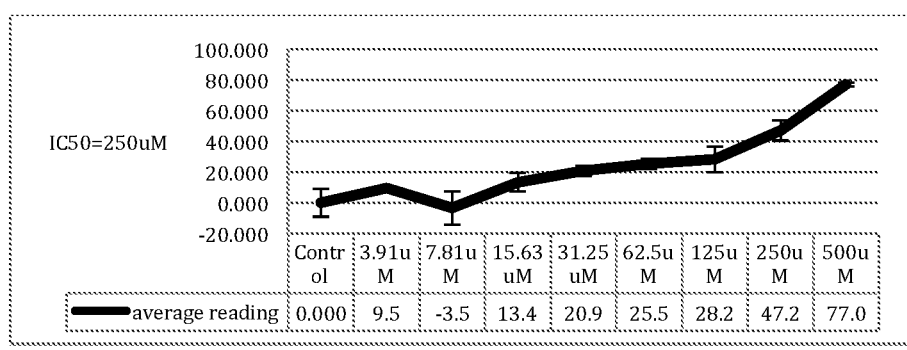
Figure 14C:
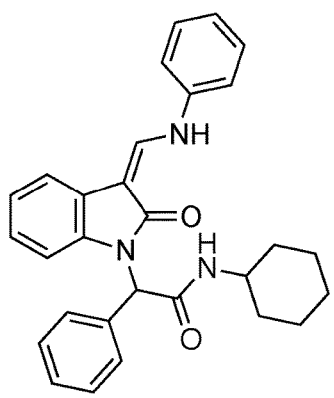
FIG. 14C shows the cell death assay (MTT assay) of (Z)—N-cyclohexyl-2-(2-oxo-3-((phenylamino)methylene)indolin-1-yl)-2-phenylacetamide with human liver stellate cells in a graph having percentage of inhibition versus concentration.
Figure 14C:
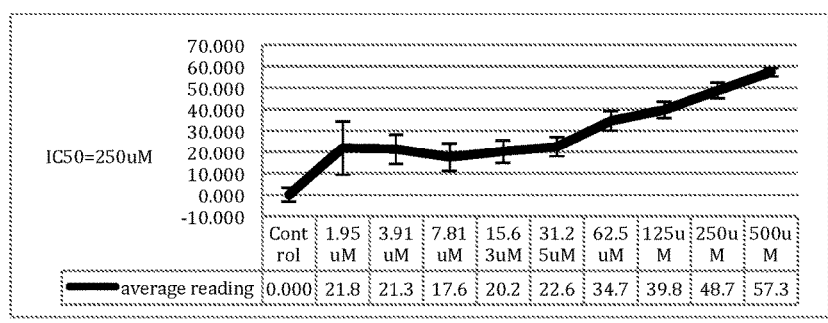
Figure 14D:
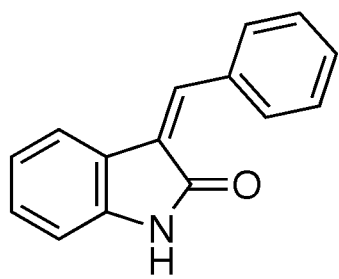
FIG. 14D shows the cell death assay (MTT assay) of (Z)-3-benzylideneindolin-2-one with human liver stellate cells in a graph having percentage of inhibition versus concentration.
Figure 14D:
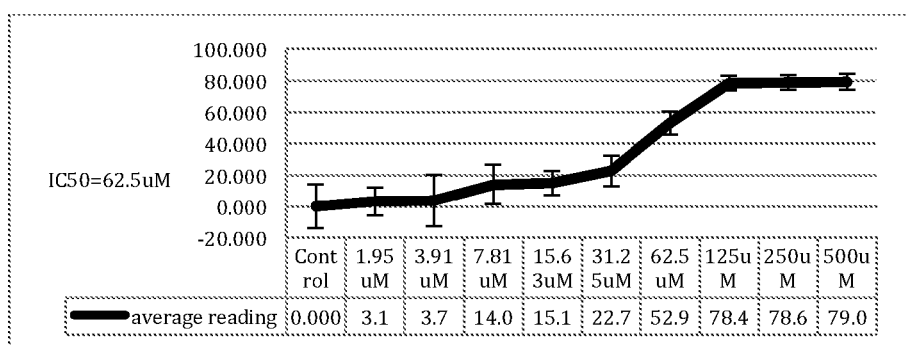
Figure 14E:
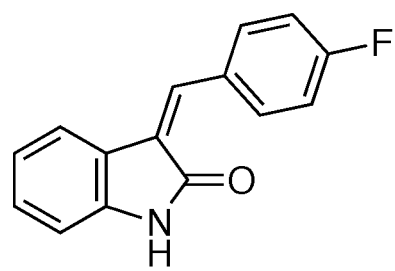
FIG. 14E shows the cell death assay (MTT assay) of (Z)-3-(4-fluorobenzylidene)indolin-2-one with human liver stellate cells in a graph having percentage of inhibition versus concentration.
Figure 14E:
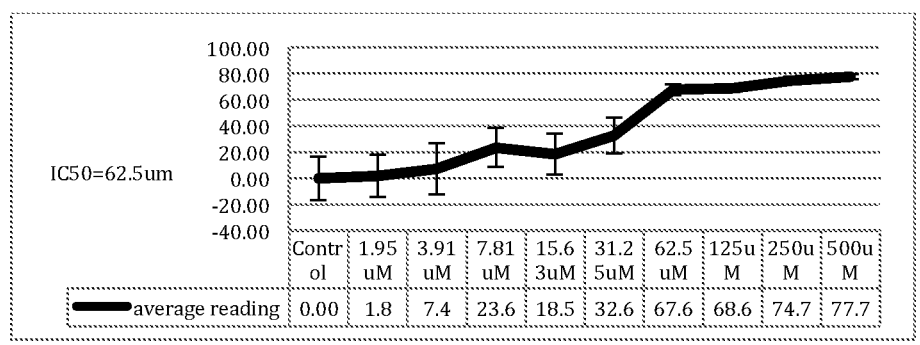
Figure 14F:
FIG. 14F shows the cell death assay (MTT assay) of (Z)-3-(4-chlorobenzylidene)indolin-2-one with human liver stellate cells in a graph having percentage of inhibition versus concentration.
Figure 14F:
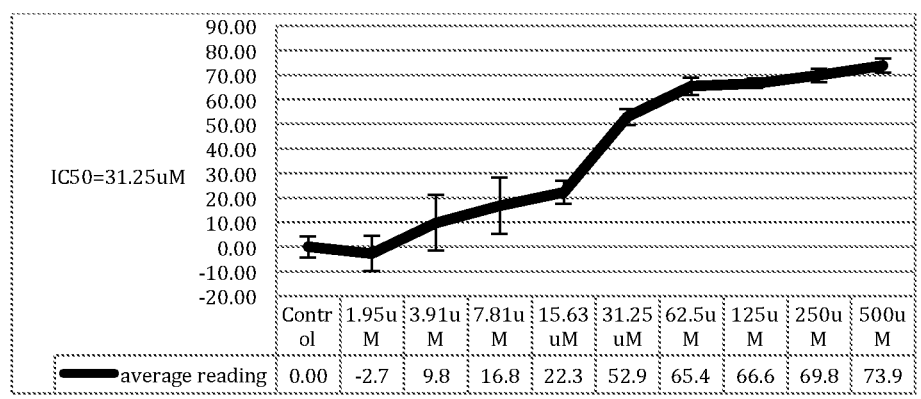
Figure 14G:
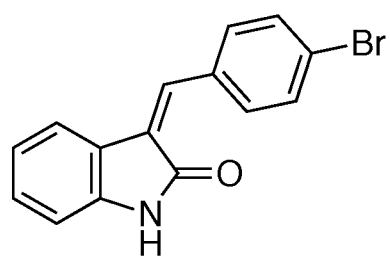
FIG. 14G shows the cell death assay (MTT assay) of (Z)-3-(4-bromobenzylidene)indolin-2-one with human liver stellate cells in a graph having percentage of inhibition versus concentration.
Figure 14G:
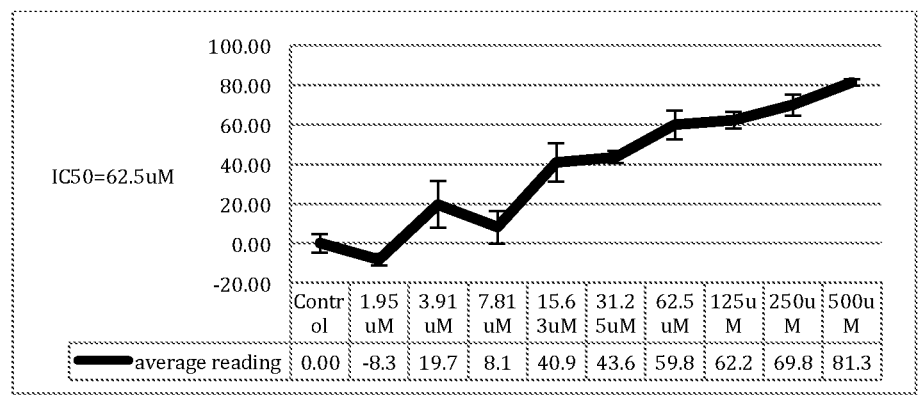
Figure 14H:
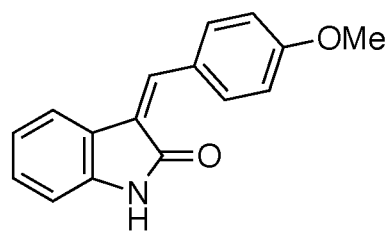
FIG. 14H shows the cell death assay (MTT assay) of (Z)-3-(4-methoxybenzylidene)indolin-2-one with human liver stellate cells in a graph having percentage of inhibition versus concentration.
Figure 14H:
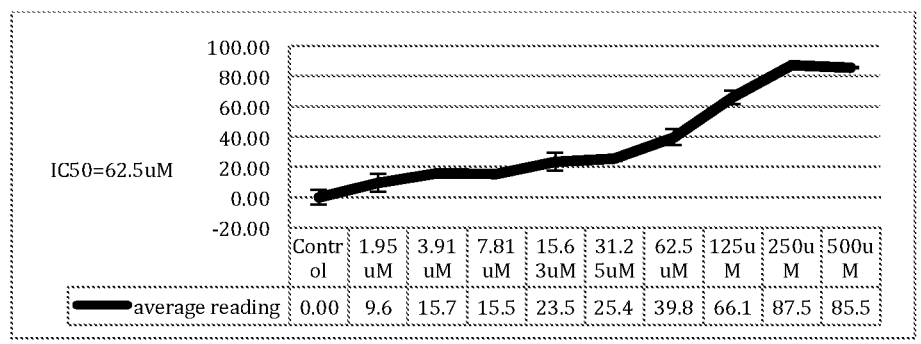
Figure 14J:
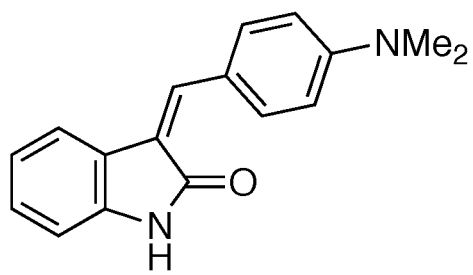
FIG. 14J shows the cell death assay (MTT assay) of (Z)-3-(4-(dimethylamino)benzylidene)indolin-2-one with human liver stellate cells in a graph having percentage of inhibition versus concentration.
Figure 14J:
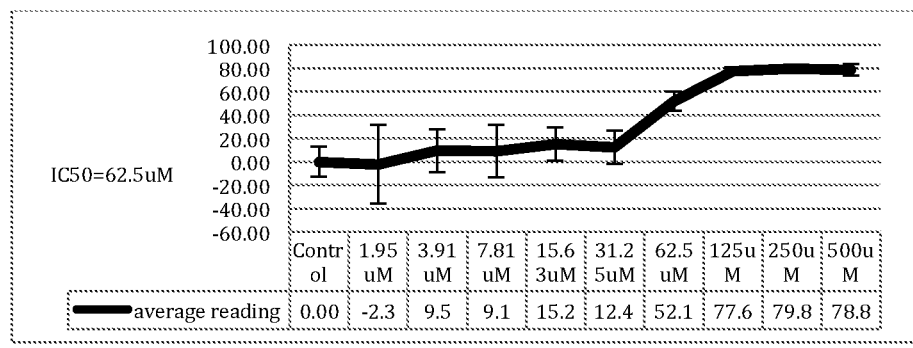
Figure 14K:
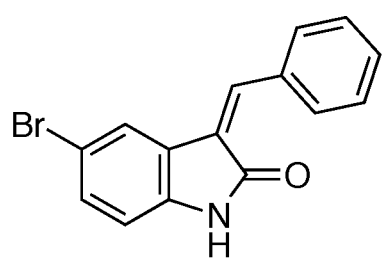
FIG. 14K shows the cell death assay (MTT assay) of (Z)-3-benzylidene-5-bromoindolin-2-one with human liver stellate cells in a graph having percentage of inhibition versus concentration.
Figure 14K:
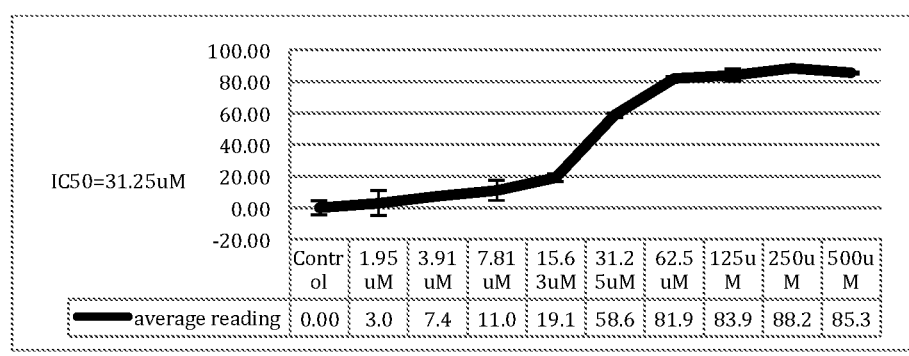
Figure 14L:
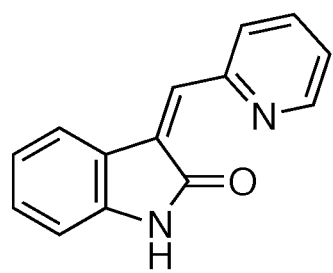
FIG. 14L shows the cell death assay (MTT assay) of (Z)-3-(pyridin-2-ylmethylene)indolin-2-one with human liver stellate cells in a graph having percentage of inhibition versus concentration.
Figure 14L:
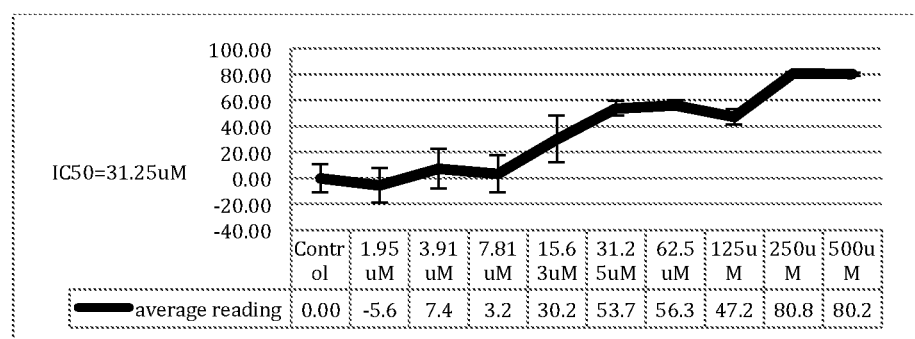
Figure 14M:
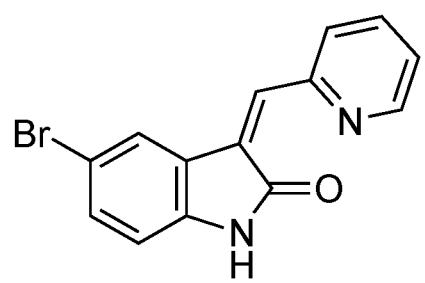
FIG. 14M shows the cell death assay (MTT assay) of (Z)-5-bromo-3-(pyridin-2-ylmethylene)indolin-2-one with human liver stellate cells in a graph having percentage of inhibition versus concentration.
Figure 14M:
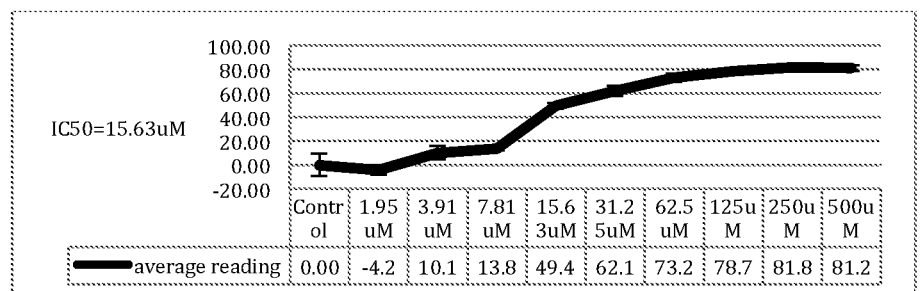
Figure 14N:
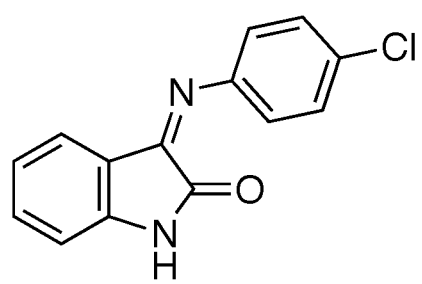
FIG. 14N shows the cell death assay (MTT assay) of (Z)-3-((4-chlorophenyl)imino)indolin-2-one with human liver stellate cells in a graph having percentage of inhibition versus concentration.
Figure 14N:
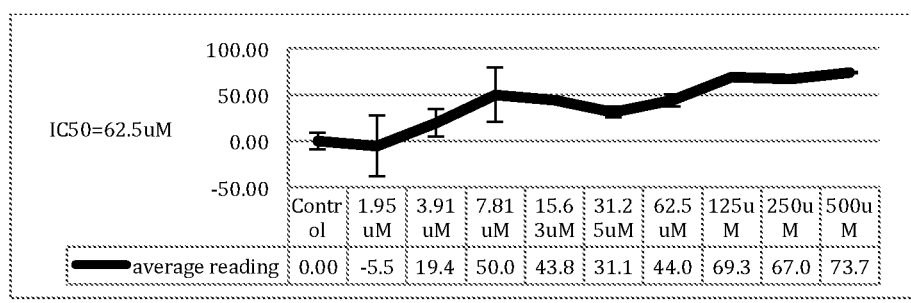
Figure 14P:
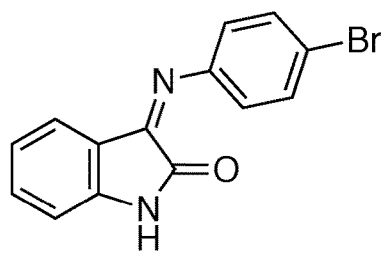
FIG. 14P shows the cell death assay (MTT assay) of (Z)-3-((4-bromophenyl)imino)indolin-2-one with human liver stellate cells in a graph having percentage of inhibition versus concentration.
Figure 14P:
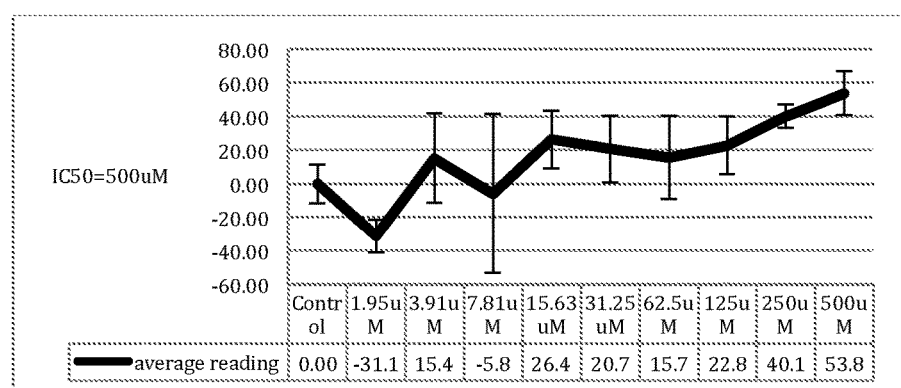
Figure 14Q:
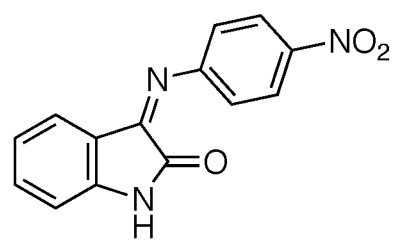
FIG. 14Q shows the cell death assay (MTT assay) of (Z)-3-((4-nitrophenyl)imino)indolin-2-one with human liver stellate cells in a graph having percentage of inhibition versus concentration.
Figure 14Q:
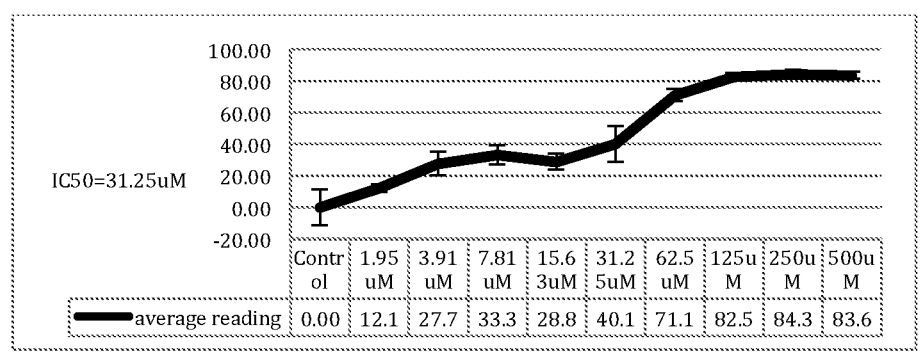
Figure 14R:
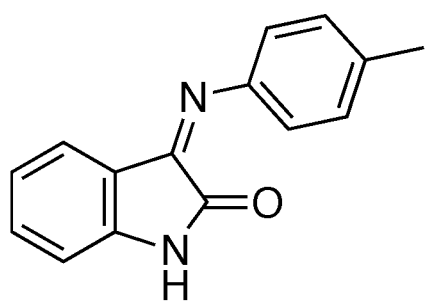
FIG. 14R shows the cell death assay (MTT assay) of (Z)-3-(p-tolylimino)indolin-2-one with human liver stellate cells in a graph having percentage of inhibition versus concentration.
Figure 14R:
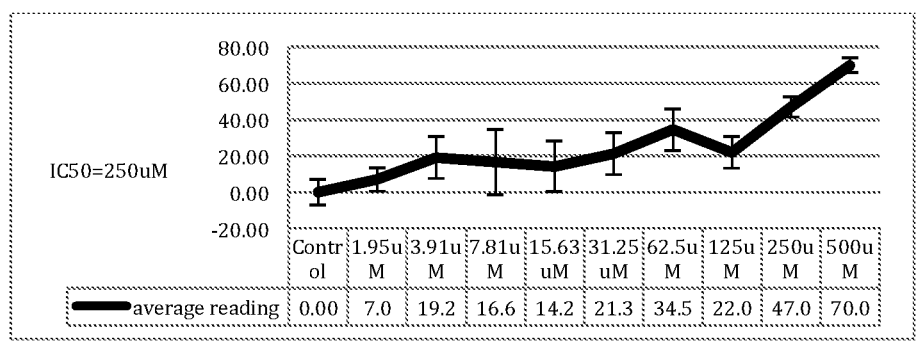
Figure 14S:
FIG. 14S shows the cell death assay (MTT assay) of (Z)-3-(pyridin-3-ylimino)indolin-2-one with human liver stellate cells in a graph having percentage of inhibition versus concentration.
Figure 14S:
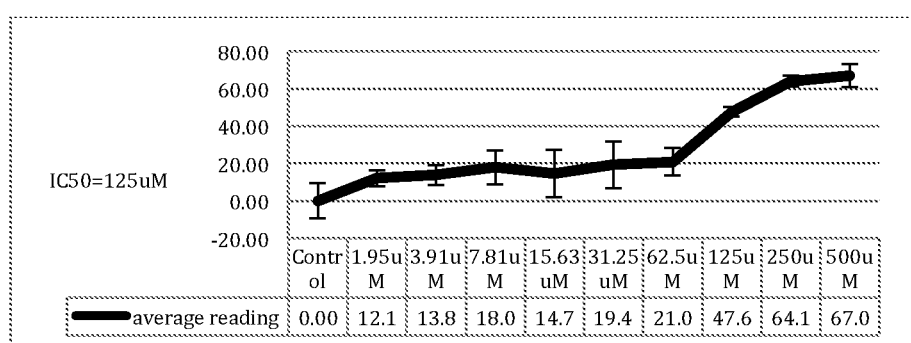
Figure 14T:
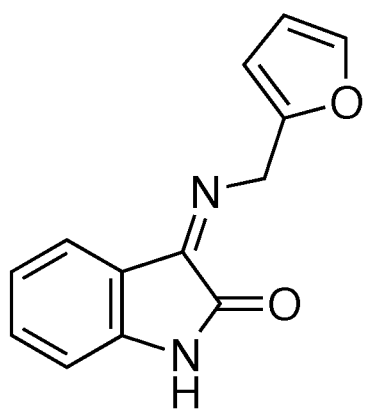
FIG. 14T shows the cell death assay (MTT assay) of (Z)-3-((furan-2-ylmethyl)imino)indolin-2-one with human liver stellate cells in a graph having percentage of inhibition versus concentration.
Figure 14T:
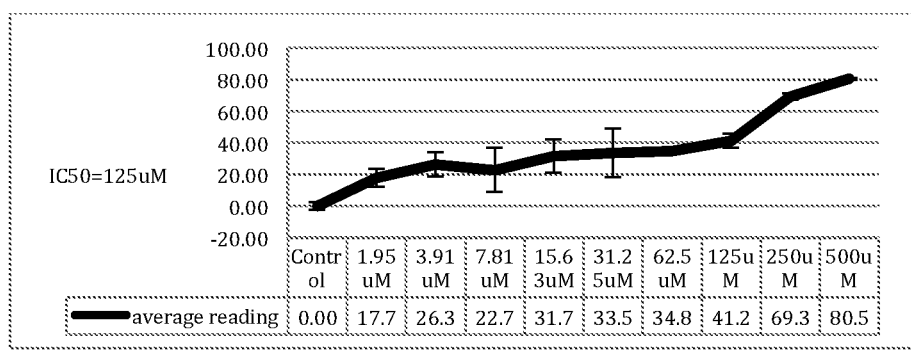

Structure-Activity Relationship (SAR) of Hesperadin Related Derivatives Using Cell-Based Screening Method Based on the cell-death assay, MTT assay, our initial SAR studies on various compounds (see FIGS. 14A through 14T) revealed that both free NH at the position 1 is generally more potent than those protected. The electronic withdrawing group (EWG) at the 5-position is also essential to remain high percentage of inhibition. General enhancement effect can be observed in exocyclic double bond with EWG at para position of aromatic substituent groups or exocyclic double bond with heteroaromatic group. Similar enhancement effects can be found in imino derivatives. Among them, Hesperadin displays very promising antifibrotic properties and representing the most potent derivative.

LIST OF REFERENCES

1. Wallace K, Burt A D, Wright M C. Liver fibrosis. Biochem J. 2008 Apr. 1; 411(1): 1-18.
2. Friedman S L. Mechanisms of hepatic fibrogenesis. Gastroenterology. 2008 May; 134(6): 1655-69.
3. Friedman S L, Bansal M B. Reversal of hepatic fibrosis-fact or fantasy? Hepatology. 2006 February; 43(2 Suppl 1): S82-8.
4. Aravalli R N, Steer C J, Cressman E N. Molecular mechanisms of hepatocellular carcinoma. Hepatology. 2008 December; 48(6): 2047-63.
5. Zhou K, Lu L G. Assessment of fibrosis in chronic liver diseases. J Dig Dis. 2009 February; 10(1): 7-14.
6. Roderfeld M, Hemmann S, Roeb E. Mechanisms of fibrinolysis in chronic liver injury (with special emphasis on MMPs and TIMPs). Z Gastroenterol. 2007 January; 45(1): 25-33.).
7. Mizuno S, Nakamura T. Hepatocyte growth factor: a regenerative drug for acute hepatitis and liver cirrhosis. Regen Med. 2007 March; 2(2): 161-70.
8. Caillot F, Hiron M, Goria O, Gueudin M, Francois A, Scotte M, Daveau M, Salier J P. Novel serum markers of fibrosis progression for the follow-up of hepatitis C virus-infected patients. Am J Pathol. 2009 July; 175(1): 46-53.
9. Koda M, Matunaga Y, Kawakami M, Kishimoto Y, Suou T, Murawaki Y. FibroIndex, a practical index for predicting significant fibrosis in patients with chronic hepatitis C. Hepatology. 2007 February; 45(2): 297-306.
10. Rani M, Yang B P, Nesbit R. Hepatitis-B control by 2012 in the WHO Western Pacific Region: rationale and implications. Bulletin World Health Organization 2009; 87:707-713.
11. NIH Consensus Development Conference: Management of Hepatitis B. http://consensus.nih.gov/2008/hepb.htm).
12. NIH Consensus Conference: Management of Hepatitis C. http://consensus.nih.gov/2002/2002HepatitisC2002116html.htm.
13. China-CDC report: http://www.chinacdc.cn/tjsj/gjwstjsj/201105/t20110504_43268.htm
14. Chan J Y, Lee K K, Chui Y L, Kuo M T. Molecular Studies. in Hepatocellular Carcinoma (ed. W. Y. Lau) World Scientific Publishing Co. Singapore, 2008, pp 243-277.
15. Chan J Y, Wang Z. Tumor Markers. In Hepatcelluar Carcinoma (ed. W. Y. Lau) World Scientific Publishing Co. Singapore, 2008, pp 159-182.
16. Cheng A S, Chan H L, Leung W K, To K F, Go M Y, Chan J Y, Liew C T, Sung J J. Expression of HBx and COX-2 in chronic hepatitis B, cirrhosis and hepatocellular carcinoma: implication of HBx in upregulation of COX-2. Mod Pathol. 2004 October; 17(10): 1169-79.
17. Chui Y L, Lee K K H, Chan J Y. BRE: Brain and Reproductive-organ Expressed gene (TNFRSF1A-modulator) 2010 Atlas of Genetics and Cytogenetics in Oncology and Haematology http://atlasgeneticsoncology.org//Genes/BREID839ch2p23.html
18. Chan J Y, Li L, Miao J, Cai D Q, Lee K K, Chui Y L. Differential expression of a novel gene BRE (TNFRSF1A modulator/BRCC45) in response to stress and biological signals. MolBiol Rep. 2010 January; 37(1):363-8.
19. Chui Y L, Ching A K, Chen S, Yip F P, Rowlands D K, James A E, Lee K K, Chan J Y. BRE over-expression promotes growth of hepatocellular carcinoma. Biochem-Biophys Res Commun. 2010 Jan. 15; 391(3):1522-5.
20. Chan B C, Ching A K, To K F, Leung J C, Chen S, Li Q, Lai P B, Tang N L, Shaw P C, Chan J Y, James A E, Lai K N, Lim P L, Lee K K, Chui Y L. BRE is an anti-apoptotic protein in vivo and over-expressed in human hepatocellular carcinoma. Oncogene 2008 27:1208-1217.
21. Tang M K, Liu G J, Chui Y L, Chan J Y, Poon T C W and Lee K K H. Livers over-expressing BRE transgene are under heightened state of stress-response, as revealed by comparative proteomics. Proteomics-Clinical Applications 2009, 3(12):1362-1370.
22. Tang M K, Wang C M, Shan S W, Chui Y L, Ching A K, Chow P H, Grotewold L, Chan J Y, Lee K K. Comparative proteomic analysis reveals a function of the novel death receptor-associated protein BRE in the regulation of prohibitin and p53 expression and proliferation. Proteomics. 2006 April; 6(8):2376-85.
23. Li Q, Ching A K, Chan B C, Chow S K, Lim P L, Ho T C, Ip W K, Wong C K, Lam C W, Lee K K, Chan J Y, Chui Y L. A death receptor-associated anti-apoptotic protein, BRE, inhibits mitochondrial apoptotic pathway. J Biol Chem. 2004 Dec. 10; 279(50):52106-16.
24. Gu C, Castellino A, Chan J Y, Chao M V. BRE: a modulator of TNF-alpha action. FASEB J. 1998 September; 12(12):1101-8.).
25. Lee K K, Kwong W H, Chau F T, Yew D T, Chan W Y. Pien Tze Huang protects the liver against carbon tetrachloride-induced damage. Pharmacol Toxicol. 2002 October; 91(4):185-92.
26. Chan W Y, Chau F T, Lee K K, Kwong W H, Yew D T. Substitution for natural musk in Pien Tze Huang does not affect its hepatoprotective activities. Hum Exp Toxicol. 2004 January; 23(1):35-47.
27. Li L L, Chan J Y, Chen S Z, Zhen Y S, Gu W L, Cai D Q, Chui Y L, Lee K K. Reversine inhibits the hyperexpression of anti-apoptotic protein BRE, TNFR[1] and autophagy protein Beclin1 in liver fibrosis in mice. Guang Dong Med J 2011 August; 32:1941-1944.
28. Lok W, Klein R Q, Saif M W. Aurora kinase inhibitors as anti-cancer therapy. Anticancer Drugs. 2010 April; 21(4):339-50.

29. Green M R, Woolery J E, Mahadevan D. Update on Aurora Kinase Targeted Therapeutics in Oncology. Drug Discov. 2011 March; 6(3):291-307.
30. Katayama H, Sen S. Aurora kinase inhibitors as anticancer molecules. Biochim Biophys Acta. 2010 October-December; 1799(10-12):829-39.
31. Cheung C H, Coumar M S, Chang J Y, Hsieh H P. Aurora kinase inhibitor patents and agents in clinical testing: an update (2009-October). Expert Opin Ther Pat. 2011 June; 21(6):857-84.
32. Coumar M S, Cheung C H, Chang J Y, Hsieh H P. Advances in Aurora kinase inhibitor patents. Expert Opin Ther Pat. 2009 March; 19(3):321-56.
33. Chen S, Zhang Q, Wu X, Schultz P G, Ding S. Dedifferentiation of lineage-committed cells by a small molecule. J Am Chem Soc. 2004 Jan. 21; 126(2): 410-1.
34. Chen S, Takanashi S, Zhang Q, Xiong W, Zhu S, Peters E C, Ding S, Schultz P G. Reversine increases the plasticity of lineage-committed mammalian cells. Proc Natl Acad Sci USA. 2007 Jun. 19; 104(25): 10482-7.
35. Kapoor T M, Lampson M A, Hergert P, Cameron L, Cimini D, Salmon E D, McEwen B F, Khodjakov A. Chromosomes can congress to the metaphase plate before biorientation. Science. 2006 Jan. 20; 311(5759):388-91.
36. Hsieh T C, Traganos F, Darzynkiewicz Z, Wu J M. The 2,6-disubstituted purine reversine induces growth arrest and polyploidy in human cancer cells. Int J Oncol. 2007 December; 31(6): 1293-300.
37. Lee E K, Bae G U, You J S, Lee J C, Jeon Y J, Park J W, Park J H, Ahn S H, Kim Y K, Choi W S, Kang J S, Han G, Han J W. Reversine increases the plasticity of lineage-committed cells toward neuroectodermal lineage. J Biol Chem. 2009 Jan. 30; 284(5): 2891-901.
38. D'Alise A M, Amabile G, Iovino M, Di Giorgio F P, Bartiromo M, Sessa F, Villa F, Musacchio A, Cortese R. Reversine, a novel Aurora kinases inhibitor, inhibits colony formation of human acute myeloid leukemia cells. Mol Cancer Ther. 2008 May; 7(5): 1140-9.
39. Shan S W, Tang M K, Chow P H, Morato M, Cai D Q and Lee K K. Induction of growth arrest and polycomb gene expression by reversine allows C2C12 cells to be reprogrammed to various differentiated cell types. Proteomics 2007; 7: 4303-26.
40. Hauf S, Cole R W, LaTerra S, Zimmer C, Schnapp G, Walter R, Heckel A, van Meel J, Rieder C L, Peters J M. The small molecule Hesperadin reveals a role for Aurora B in correcting kinetochore-microtubule attachment and in maintaining the spindle assembly checkpoint. J Cell Biol. 2003 Apr. 28; 161(2):281-94.).
41. Jetton N, Rothberg K G, Hubbard J G, Wise J, Li Y, Ball H L, Ruben L. The cell cycle as a therapeutic target against Trypanosomabrucei: Hesperadin inhibits Aurora kinase-1 and blocks mitotic progression in bloodstream forms. Mol Microbiol. 2009 April; 72(2):442-58.).
42. Sessa F, Mapelli M, Ciferri C, Tarricone C, Areces L B, Schneider T R, Stukenberg P T, Musacchio A. Mechanism of Aurora B activation by INCENP and inhibition by Hesperadin. Mol Cell. 2005 Apr. 29; 18(3):379-91.
43. Amabile G, D'Alise A M, Iovino M, Jones P, Santaguida S, Musacchio A, Taylor S, Cortese R. The Aurora B kinase activity is required for the maintenance of the differentiated state of murine myoblasts. Cell Death Differ. 2009 February; 16(2):321-30.
44. Agnese V, Bazan V, Fiorentino F P, Fanale D, Badalamenti G, Colucci G, Adamo V, Santini D, Russo A. The role of Aurora-A inhibitors in cancer therapy. Ann Oncol. 2007 June; 18Suppl 6:vi47-52.
45. Wang W, Stukenberg P T, Brautigan D L. Phosphatase inhibitor-2 balances protein phosphatase 1 and aurora B kinase for chromosome segregation and cytokinesis in human retinal epithelial cells. MolBiol Cell. 2008 November; 19(11):4852-62.
46. Hivert V, Pierre J, Raingeaud J. Phosphorylation of human enhancer of filamentation (HEF1) on serine 369 induces its proteasomal degradation. Biochem Pharmacol. 2009 Oct. 15; 78(8):1017-25.
47. Dreier M R, Grabovich A Z, Katusin J D, Taylor W R. Short and long-term tumor cell responses to Aurora kinase inhibitors. Exp Cell Res. 2009 Apr. 15; 315(7):1085-99.
48. Dobrynin G, Popp O, Romer T, Bremer S, Schmitz M H, Gerlich D W, Meyer H. Cdc48/p97-Ufd1-Npl4 antagonizes Aurora B during chromosome segregation in HeLa cells. J Cell Sci. 2011 May 1; 124(Pt 9):1571-80.
49. Keerthivasan G, Small S, Liu H, Wickrema A, Crispino J D. Vesicle trafficking plays a novel role in erythroblast enucleation. Blood. 2010 Oct. 28; 116(17):3331-40.
50. Demidov D, Hesse S, Tewes A, Rutten T, Fuchs J, Ashtiyani R K, Lein S, Fischer A, Reuter G, Houben A. Auroral phosphorylation activity on histone H3 and its cross-talk with other post-translational histone modifications in *Arabidopsis*. Plant J. 2009 July; 59(2):221-30.
51. Kurihara D, Matsunaga S, Uchiyama S, Fukui K. Live cell imaging reveals plant aurora kinase has dual roles during mitosis. Plant Cell Physiol. 2008 August; 49(8): 1256-61.
52. Kurihara D, Matsunaga S, Kawabe A, Fujimoto S, Noda M, Uchiyama S, Fukui K. Aurora kinase is required for chromosome segregation in tobacco BY-2 cells. Plant J. 2006 November; 48(4):572-80.
53. Sakita-Suto S, Kanda A, Suzuki F, Sato S, Takata T, Tatsuka M. Aurora-B regulates RNA methyltransferase NSUN2. Mol Biol Cell. 2007 March; 18(3):1107-17.
54. Green M R, Woolery J E, Mahadevan D. Update on Aurora Kinase Targeted Therapeutics in Oncology. Drug Discov. 2011 March; 6(3):291-307.
55. U.S. Patent Publication 2010/0204211 MEDICAMENTS FOR THE TREATMENT OR PREVENTION OF FIBROTIC DISEASES.
56. U.S. Patent Publication 2009/0048267 MEDICAMENTS FOR THE TREATMENT OR PREVENTION OF FIBROTIC DISEASES.
57. U.S. Patent Publication 2006/0154939 MEDICAMENTS FOR THE TREATMENT OR PREVENTION OF FIBROTIC DISEASES
58. U.S. Patent Publication 2006/0148883 MEDICAMENTS FOR THE TREATMENT OR PREVENTION OF FIBROTIC DISEASES.
59. U.S. Patent Publication 2006/0142373 MEDICAMENTS FOR THE TREATMENT OR PREVENTION OF FIBROTIC DISEASES
60. Walter, R., A. Heckel, G. J. Roth, J. Kley, G. Schnapp, M. Lenter, J. C. A. van Meel, W. Spevak, and U. Weyer-Czernilofsky. 2002 May 10. Sulfonylamino substituted 3-(aminomethylide)-2-indolinones as cell proliferation inhibitors. Patent Cooperation Treaty Application PCT/EP2001/012523, International Publication Number WO 2002/036564 A1.
61. Sato Y, Murase K, Kato J, Kobune M, Sato T, Kawano Y, Takimoto R, Takada K, Miyanishi K, Matsunaga T, Takayama T, Niitsu Y. Resolution of liver cirrhosis using vitamin A-coupled liposomes to deliver siRNA against a collagen-specific chaperone. Nature Biotechnology 2008 26 (4) 431-442.

62. Riccalton-Banks L, Bhandari R, Fry J, Shakesheff K M. A simple method for the simultaneous isolation of stellate cells and hepatocytes from rat liver tissue. Mol Cell Biochem 2003 June 248(1-2):97-102.
63. Yata Y, Enosawa S, Suzuki S, Li X K, Tamura A, Kimura H, Takahara T, Watanabe A. An improved method for the purification of stellate cells from rat liver with dichloromethylenediphosphate (CL2MDP). Methods Cell Sci. 1999 21(1):19-24.
64. Tang, J. C. O.; Chan, A. S. C.; Lam, K. H.; Chui, C. H.; Kok, S. H. L.; Yuen, M. C. W.; Chan S. H.; Cheng, C. H.; Cheung, F. Water-Soluble Polymer-Based Cantharimides as Potentially Selective Anti-tumor Agents, U.S. Patent Publication US2010/0273840.

What is claimed is:

1. A method for treating liver fibrosis, comprising:
preparing a compound, a tautomer, a stereoisomer, a pharmaceutically acceptable salt or ester thereof, wherein the compound is a member selected from the group consisting of:
(Z)—N-(2-oxo-3-(phenyl(4-(piperidin-1-ylmethyl)phenylamino)methylene)indolin-5-yl)ethanesulfonamide (Hesperadin),
(Z)—N-cyclohexyl-2-(2-oxo-3-(phenyl(phenylamino) methylene)indolin-1-yl)-2-phenylacetamide,
(Z)—N-cyclohexyl-2-(2-oxo-3-((phenylamino)methylene)indolin-1-yl)-2-phenylacetamide,
(Z)-3-benzylideneindolin-2-one,
(Z)-3-(4-fluorobenzylidene)indolin-2-one,
(Z)-3-(4-chlorobenzylidene)indolin-2-one,
(Z)-3-(4-bromobenzylidene)indolin-2-one,
(Z)-3-(4-methoxybenzylidene)indolin-2-one,
(Z)-3-(4-(dimethylamino)benzylidene)indolin-2-one,
(Z)-3-benzylidene-5-bromoindolin-2-one,
(Z)-3-(pyridin-2-ylmethylene)indolin-2-one,
(Z)-5-bromo-3-(pyridin-2-ylmethylene)indolin-2-one,
(Z)-3-((4-chlorophenyl)imino)indolin-2-one,
(Z)-3-((4-bromophenyl)imino)indolin-2-one,
(Z)-3-((4-nitrophenyl)imino)indolin-2-one,
(Z)-3-(p-tolylimino)indolin-2-one,
(Z)-3-(pyridin-3-ylimino)indolin-2-one, and
(Z)-3-((furan-2-ylmethyl)imino)indolin-2-one;
administering an effective amount of the compound to a subject having liver fibrosis;
targeting hepatic stellate cells of the subject;
inhibiting synthesis or expression of at least one collagen or extra cellular matrix proteins; and
reversing the liver fibrosis.

2. The method according to claim 1, wherein the compound is (Z)—N-(2-oxo-3-(phenyl(4-(piperidin-1-ylmethyl) phenylamino)methylene)indolin-5-yl)ethanesulfonamide.

3. The method according to claim 1, wherein the at least one collagen is selected from the group consisting of collagen type I, collagen type III, collagen type IV, collagen type V, collagen type VI and collagen type VII.

4. The method according to claim 2, wherein the at least one collagen is selected from the group consisting of collagen type I, collagen type III, collagen type IV, collagen type V, collagen type VI and collagen type VII.

\* \* \* \* \*

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Completely Synthesized

<400> SEQUENCE: 1
acacgtctcg gtcatggta                                                  19

<210> SEQ ID NO 2
<211> LENGTH: 19
<212> TYPE: DNA
<213> ORGANISM: Artificial Sequence
<220> FEATURE:
<223> OTHER INFORMATION: Completely Synthesized

<400> SEQUENCE: 2
agaggaaggc caagtcgag                                                  19

<210> SEQ ID NO 3
<211> LENGTH: 19
<212> TYPE: DNA
<213> ORGANISM: Artificial Sequence
<220> FEATURE:
<223> OTHER INFORMATION: Completely Synthesized

<400> SEQUENCE: 3
ggactgacca agatgggaa                                                  19

<210> SEQ ID NO 4
<211> LENGTH: 19
<212> TYPE: DNA
<213> ORGANISM: Artificial Sequence
<220> FEATURE:
<223> OTHER INFORMATION: Completely Synthesized

<400> SEQUENCE: 4
ggggagctgg ctacttctc                                                  19

<210> SEQ ID NO 5
<211> LENGTH: 19
<212> TYPE: DNA
<213> ORGANISM: Artificial Sequence
<220> FEATURE:
<223> OTHER INFORMATION: Completely Synthesized

<400> SEQUENCE: 5
gaaagccagg atccatttt                                                  19

<210> SEQ ID NO 6
<211> LENGTH: 18
<212> TYPE: DNA
<213> ORGANISM: Artificial Sequence
```

```
<220> FEATURE:
<223> OTHER INFORMATION: Completely Synthesized

<400> SEQUENCE: 6 tgccgcctttt aactggag                                          18

<210> SEQ ID NO 7
<211> LENGTH: 19
<212> TYPE: DNA
<213> ORGANISM: Artificial Sequence
<220> FEATURE:
<223> OTHER INFORMATION: Completely Synthesized

<400> SEQUENCE: 7
tggtccacct ggttcaact                                          19

<210> SEQ ID NO 8
<211> LENGTH: 19
<212> TYPE: DNA
<213> ORGANISM: Artificial Sequence
<220> FEATURE:
<223> OTHER INFORMATION: Completely Synthesized

<400> SEQUENCE: 8
cgacgtcttc cagtaccga                                          19

<210> SEQ ID NO 9
<211> LENGTH: 19
<212> TYPE: DNA
<213> ORGANISM: Artificial Sequence
<220> FEATURE:
<223> OTHER INFORMATION: Completely Synthesized

<400> SEQUENCE: 9
acttggccct gatgacgag                                          19

<210> SEQ ID NO 10
<211> LENGTH: 20
<212> TYPE: DNA
<213> ORGANISM: Artificial Sequence
<220> FEATURE:
<223> OTHER INFORMATION: Completely Synthesized

<400> SEQUENCE: 10
ctgttgttgc tgtggctgat                                         20
```